US012734343B1

(12) United States Patent
Hakim

(10) Patent No.: US 12,734,343 B1
(45) Date of Patent: Sep. 15, 2026

(54) METHOD OF DIAGNOSING PHYSIOLOGICAL DISORDERS OF THE CENTRAL NERVOUS SYSTEM

(71) Applicant: Carlos A. Hakim, Coconut Grove, FL (US)

(72) Inventor: Carlos A. Hakim, Coconut Grove, FL (US)

( * ) Notice: Subject to any disclaimer, the term of this patent is extended or adjusted under 35 U.S.C. 154(b) by 58 days.

(21) Appl. No.: 17/375,849

(22) Filed: Jul. 14, 2021

Related U.S. Application Data

(63) Continuation of application No. 15/981,212, filed on May 16, 2018, now abandoned, which is a continuation of application No. 14/208,754, filed on Mar. 13, 2014, now abandoned.

(60) Provisional application No. 61/790,587, filed on Mar. 15, 2013.

(51) Int. Cl.

| | |
|---|---|
| ***A61M 27/00*** | (2006.01) |
| ***A61B 1/06*** | (2006.01) |
| ***A61B 5/00*** | (2006.01) |
| ***A61B 5/03*** | (2006.01) |
| ***A61B 5/1455*** | (2006.01) |
| ***A61G 10/02*** | (2006.01) |
| ***A61M 37/00*** | (2006.01) |
| ***A61P 25/00*** | (2006.01) |

(52) U.S. Cl.
CPC ............. *A61M 27/002* (2013.01); *A61B 1/06* (2013.01); *A61B 5/031* (2013.01); *A61B 5/14553* (2013.01); *A61B 5/4064* (2013.01); *A61G 10/026* (2013.01); *A61M 37/00* (2013.01); *A61P 25/00* (2018.01)

(58) Field of Classification Search
CPC ....... A61M 27/002; A61M 37/00; A61B 1/06; A61B 5/4064; A61B 5/031; A61B 5/14553; A61G 10/026; A61P 25/00
See application file for complete search history.

(56) References Cited

U.S. PATENT DOCUMENTS

| | | | |
|---|---|---|---|
| 3,288,142 | A | 11/1966 | Hakim |
| 3,516,410 | A | 6/1970 | Hakim |
| 3,527,226 | A | 9/1970 | Hakim |
| 3,877,137 | A | 4/1975 | Hakim et al. |
| 3,886,948 | A | 6/1975 | Hakim |
| 3,889,687 | A | 6/1975 | Harris et al. |
| 3,958,562 | A | 5/1976 | Hakim et al. |
| 4,106,510 | A | 8/1978 | Hakim et al. |
| 4,312,293 | A | 1/1982 | Hakim |
| 4,332,255 | A | 6/1982 | Hakim et al. |
| 4,387,715 | A | 6/1983 | Hakim et al. |
| 4,551,128 | A | 11/1985 | Hakim et al. |
| 4,595,390 | A | 6/1986 | Hakim et al. |
| 4,608,992 | A | 9/1986 | Hakim et al. |
| 4,615,691 | A | 10/1986 | Hakim et al. |
| 4,772,257 | A | 9/1988 | Hakim et al. |
| 5,772,607 | A | 6/1998 | Magram |
| 5,928,182 | A | 7/1999 | Kraus et al. |
| 6,455,494 | B1 | 9/2002 | Jefferies et al. |
| 7,309,330 | B2 | 12/2007 | Bertrand et al. |
| 8,008,492 | B2 | 8/2011 | Lledo et al. |
| 8,026,209 | B2 | 9/2011 | Gaillard et al. |
| 8,124,095 | B2 | 2/2012 | Pardridge et al. |
| 8,142,781 | B2 | 3/2012 | Pardridge et al. |
| 8,242,088 | B2 | 8/2012 | Joliot et al. |
| 8,383,107 | B2 | 2/2013 | Muruganandam et al. |
| 8,535,656 | B2 | 9/2013 | Kabanov et al. |
| 8,545,812 | B2 | 10/2013 | Hong et al. |
| 8,546,319 | B2 | 10/2013 | Starr et al. |
| 8,609,103 | B2 | 12/2013 | Zankel et al. |
| 8,613,929 | B2 | 12/2013 | Gaillard et al. |
| 8,629,114 | B2 | 1/2014 | Walz |
| 8,637,648 | B1 | 1/2014 | Mash et al. |
| 2009/0130019 | A1 | 5/2009 | Tobinick |
| 2012/0315282 | A1 | 12/2012 | Bedinger et al. |

OTHER PUBLICATIONS

Olsson et al. [abstract only] Alzheimer's & Dementia, vol. 10, Issue 5S: S374-S380, Dec. 12, (Year: 2013).*
Varma et al., Eye, 27:688-697, Mar. 8 (Year: 2013).*
Tian et al. Clinical effect of Exelon and the high pressure oxygen uniting to treat the elderly dementia and influence of Exelon on plasma TGF-β, IGF-1 and ICAM-1 in patients with elderly dementia. J. Clin. Neurol. 20, 32-34 (Year: 2007).*
Lin et al. Front. Aging Neurosci. 16:1360148, (Year: 2024).*
Nazir et al. J of AAPOS, vol. 13, No. 1, (Year: 2009).*
Czosnyka et al., Acta Neurochir, [Suppl] 81: 27-30. (Year: 2002).*
Jones, et al., "Hydrocephalus 2008, Sep. 17-20, Hannover Germany: a conference report," 16, Cerebrospinal Fluid Research 5:19 (2008).
Shprecher, et al., Normal Pressure Hydrocephalus: Diagnosis and Treatment, Current Neurology & Neuroscience Reports 8:5, pp. 371-376 (2008).

(Continued)

*Primary Examiner* — Stacey N MacFarlane
(74) *Attorney, Agent, or Firm* — Lando & Anastasi, LLP

(57) ABSTRACT

The invention is directed to a method of treating a patient suffering from a disorder of the central nervous system comprising administering to said patient a pharmacologic agent that increases the flexibility of the walls of the veins and/or arteries, or both, in the subarachnoid space of the brain. The invention also encompasses a method comprising administering to said patient a pharmacologic agent that increases the flexibility of the veins and/or arteries, or both, further comprising implanting a shunt that decreases CSF pressure in the brain of said patient. The invention additionally encompasses a method comprising administering to said patient a pharmacologic agent that increases the flexibility of the veins and/or arteries, or both, further comprising increasing the venous pressure of the brain. In yet another aspect, the invention is directed to a method of treating a patient suffering from a central nervous system disorder comprising introducing said patient into a hyperbaric environment.

15 Claims, 22 Drawing Sheets

(56) References Cited

OTHER PUBLICATIONS

Goldstein, et al., "Phorbol Ester-induced Inhibition of Collagen Accumulation by Human Lung Fibroblasts", The Journal of Biological Chemistry 265:23 pp. 13623-13628 (1990).
Nwogu, et al., "Inhibition of Collagen Synthesis With Prolyl 4-Hydroxylase Inhibitor Improves Left Ventrical Function and Alters the Patter of Left Ventricular Dilatation After Myocardial Infarction" Circulation 104, pp. 2216-2221 (2001).
Pischon, et al., "Regulation of Collagen Deposition and Lysyl Oxidase by Tumor Necrosis Factor in Osteoblasts" The Journal of Biological Chemistry 279:29, pp. 30060-30065 (2004).
Hakim et al., "Normal-Pressure Hydrocephalus" Neurosurgery Clinics of North America, vol. 36, No. 4 pp. 761-773 (2001).
Baechli et al., "Hyperbaric Oxygen Therapy (HBO) for the Treatment of an Epidural Abscess in the Posterior Fossa In an 8-Month-Old Infant", Pediatric Neurosurgery, 2008; 44:239-242.
Sajanti et al., "Rapid Induction of Meningeal Collagen Synthesis in the Cerebral Cisternal and Ventricular Compartments after Subarachnoid Hemorrhage", Acta Neurochir. (Wien), 2001, pp. 821-826.
Weaver, Lindell, "Hyperbaric Medicine for the Hospital-Based Physician", Hospital Practice, 2012, vol. 40, pp. 88-101 (Abstract only).
Zhi et al., Hyperbaric oxygenation therapy of Normal Pressure Hydrocephalus, European Underwater and Baromedical Society, Annual Meeting Abstract S.217, Sep. 4-8, 1996.
Gabb et al., "Hyperbaric Oxygen* a Therapy in Search of Diseases", Chest, 92(6):1074-1082, 1987.
Canham et al., " Layered collagen fabric of cerebral aneurysms quantitatively assessed by the universal stage and polarized light microscopy", The Anatomical Record, 231 :579-592, 1991.
MacDonald et al. Annals Biomed Engin., 28:533-542, 2000.
Fleckenstein et al., "This technology is relatively easy and non-invasive, but can be a valuable asset in diagnosing retinal disease", Rev of Opthal., Aug. 12, 2010.
Whittaker et al., "The Molecular Organization of Collagen in Saccular Aneurysms Assessed by Polarized Light Microscopy", Connective Tissue Res. 17(1):43-54, 1988.
Hakim The Physics and Physicopathology of the Hydraulic Complex of the Central Nervous System (The Mechanics of Hydrocephalus and Normal Pressure Hydrocephalus), Massachusetts Institute of Technology. pp. 1-157 (1985).
Marshall et al., Ultrastructural distribution of collagen types I-VI in aging human retinal vessels. British Journal of Ophthalmology, 1990,74,228-232.
Bueno et al., Enhancement of confocal microscopy images using Mueller-matrix polarimetry. Journal of Microscopy, vol. 235, Pt 1 2009, pp. 84-93.
Rockswold et al., A prospective, randomized clinical trial to compare the effect of hyperbaric to normobaric hyperoxia on cerebral metabolism, intracranial pressure, and oxygen toxicity in severe traumatic brain injury. J Neurosurg 112:1080-1094, 2010.
Julow et al., Polarization Microscopic Investigation of Subarachnoid Fibrosis after Subarachnoid Haemorrhage. Acta Neurochirurgica 53, 237-245 (1980).
Motohashi et al., Subarachnoid Haemorrhage Induced Proliferation of Leptomeningeal Cells and Deposition of Extracellular Matrices in the Arachnoid Granulations and Subarachnoid Space. Acta Neurochir (Wien) (1995) 136:88-91.
Tobinick et al., TNF-alpha Modulation for Treatment of Alzheimer's Disease: A 6-Month Pilot Study. MedGenWed. 2006; 8(2): 25.
Li et al., Myocardial extracellular matrix remodeling in transgenic mice overexpressing tumor necrosis factor alpha can be modulated by anti-tumor necrosis factor a therapy. 12746-12751 u PNAS u Nov. 7, 2000 u vol. 97 u No. 23.
Kohsi et al., "Intracranial Pressure Responses During Hyperbaric Oxygen Therapy" Neurol Med Chir (Tokyo) 1991, 31: pp. 575-581.
Berisha et al., "Retinal Abnormalities in Early Alzheimer's Disease" IOVS 2007, 48: pp. 2285-2289.
McGrory et al., "The application of retinal fundus camera imaging in dementia: A systematic review" Alzheimer's & Dementia, Assessment & Disease Monitoring 2017, 6: pp. 91-107.
Tarkowski et al., "Normal pressure hydrocephalus triggers intrathecal production of TNF-alpha", Neurobiology of Aging, vol. 24, 2003, pp. 707-714.
Bateman et al., "The role of altered impedance in the pathophysiology of normal pressure hydrocephalus, Alzheimer's disease and syringomyelia", Medical Hypotheses, vol. 63, 2004, pp. 980-985.
Li et al., "Expression of TGF betas and TGF beta type II receptor in cerebrospinal fluid of patients with idiopathic normal pressure hydrocephalus", Neuroscience Letters, vol. 413, 2007, pp. 141-144.
Tada et al., "Intraventricular administration of hepatocyte growth factor treats mouse communicating hydrocephalus Induced by transforming growth factor 81", Neurobiology of Disease, vol. 21, 2006, pp. 576-586.
Park et al., "Accuracy and Safety of Bedside External Ventricular Drain Placement at Two Different Cranial Sites: Kocher's Point versus Forehead" J Korean Neurosurg Soc 50, pp. 317-321, 2011.
Rhodin, "Architecture of the vessel wall," in Berne, Ed. Vol. 2, American Phsiology Society, Bethesda, MD: 1979 (Handbook of Physiology) Chapter 1, Sect. 2, 1-31.
Schneiderman, "The Funduscopic Examination, Clinical Methods: The History, Physical, and Laboratory Examinations," 3rd Edition, Walker et al., Eds. Boston, MA: Butterworths; 1990; Chapter 117.
Evans, "Polarized Light Attachment for Opthalmoscopy," From the Department of Ophthamology, Long Island College of Medicine (1936), pp. 113-117.
Chakravarty, "Unifying concept for Alzheimer's disease, vascular dementia and normal pressure hydrocephalus—a hypothesis," Medical Hypotheses (2004) 63, pp. 827-833.
Li et al., "Effect of hepatocyte growth factor encapsulated in targeted liposomes on liver cirrhosis," Journal of Controlled Release vol. 131, Issue 1, Oct. 6, 2008, pp. 77-82.

* cited by examiner

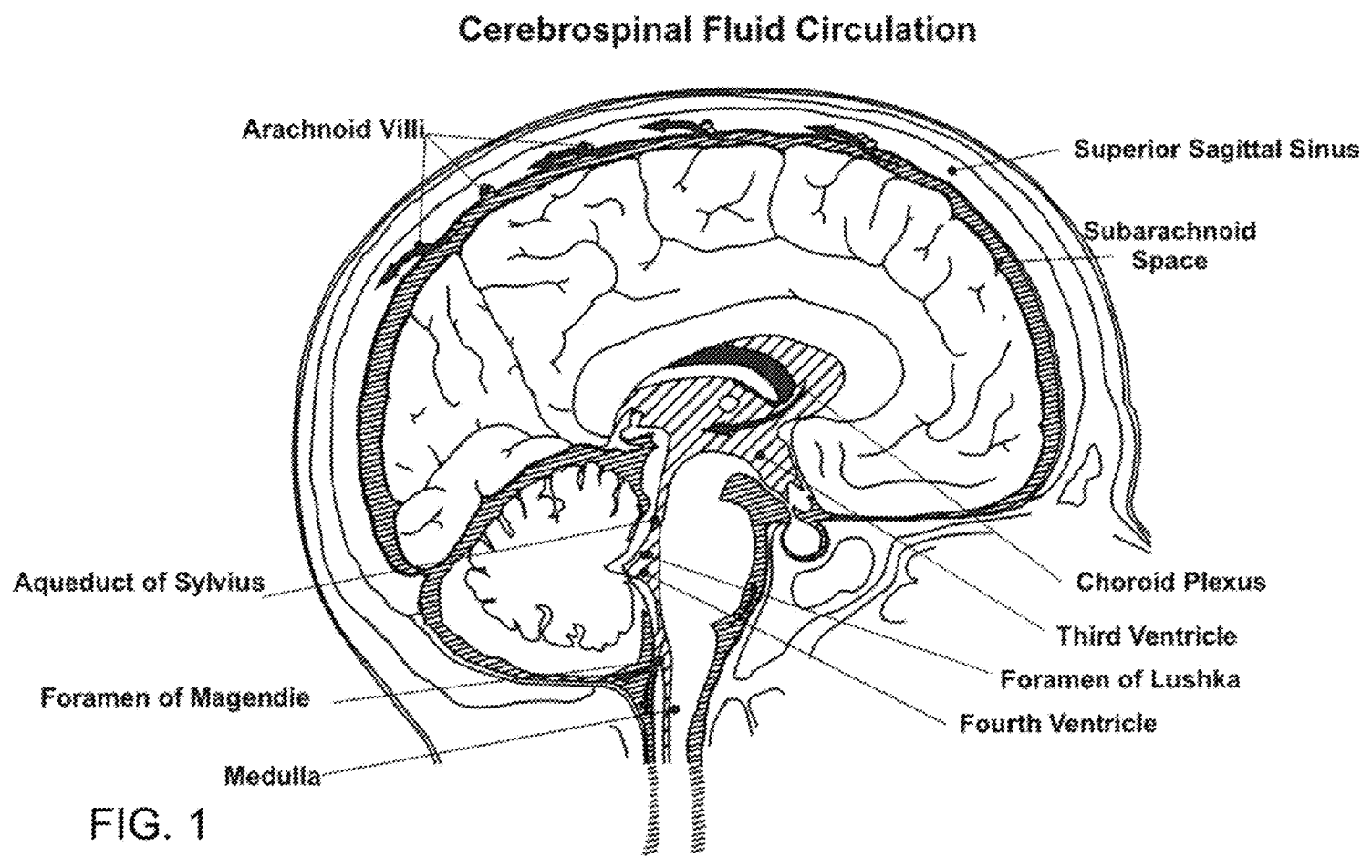

Cerebrospinal Fluid Circulation

Superior Sagittal Sinus
Subarachnoid Space
Choroid Plexus
Third Ventricle
Foramen of Lushka
Fourth Ventricle
Arachnoid Villi
Aqueduct of Sylvius
Foramen of Magendie
Medulla

FIG. 1

FIG. 8B Hydrocephalic Brain
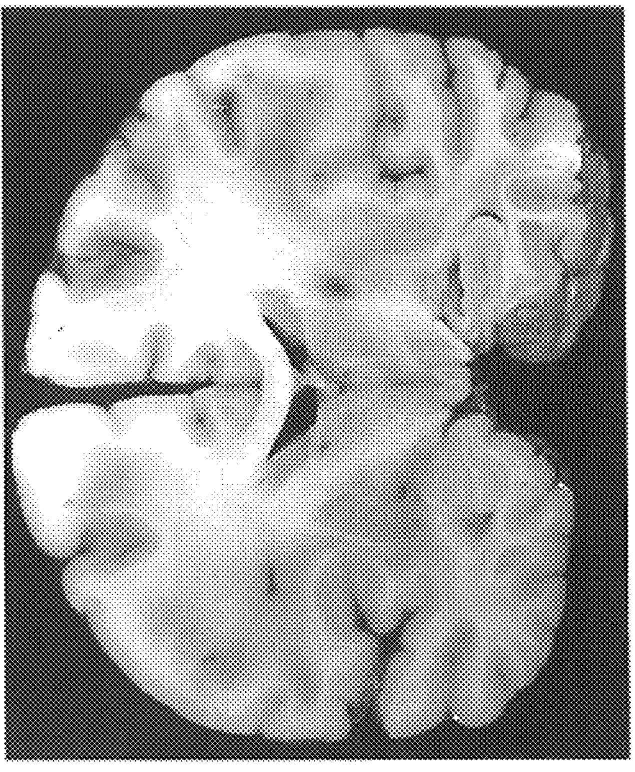
FIG. 8A Normal Brain

Normal Light | Polarized Light
FIG. 14A Normal Brain
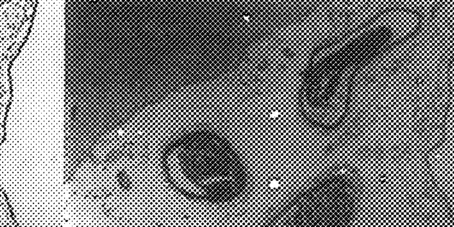
FIG. 14B High Pressure Hydrocephalus
FIG. 14C Normal Pressure Hydrocephalus
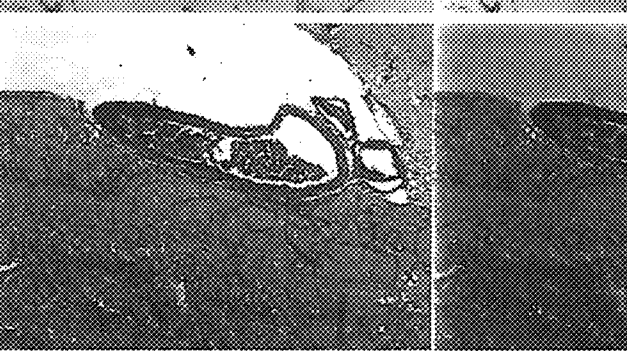
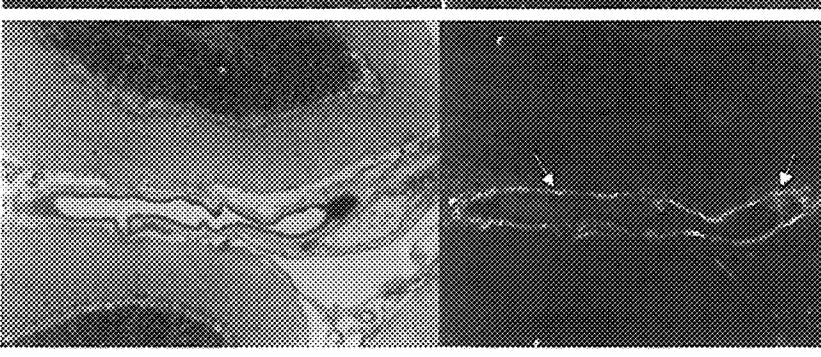
Cross section through Subarachnoid veins as seen under the microscope. Only the adventitia of the Subarachnoid vessels in Normal Pressure Hydrocephalus show optical activity under polarized light.

METHOD OF DIAGNOSING PHYSIOLOGICAL DISORDERS OF THE CENTRAL NERVOUS SYSTEM

CROSS REFERENCE TO RELATED APPLICATIONS

This application claims priority under 35 U.S.C. § 120 as a continuation of U.S. patent application Ser. No. 17/375,849, titled "METHOD OF TREATING PHYSIOLOGICAL DISORDERS OF THE CENTRAL NERVOUS SYSTEM," filed Jul. 14, 2021, which is a continuation of U.S. patent application Ser. No. 15/981,212, titled "METHOD OF TREATING PHYSIOLOGICAL DISORDERS OF THE CENTRAL NERVOUS SYSTEM," filed May 16, 2018, which is a continuation of U.S. patent application Ser. No. 14/208,754, titled "METHOD OF TREATING PHYSIOLOGICAL DISORDERS OF THE CENTRAL NERVOUS SYSTEM," filed Mar. 13, 2014, which claims priority from U.S. Ser. No. 61/790,587, filed Mar. 15, 2013. Each of these applications is herein incorporated by reference in its entirety for all purposes.

BACKGROUND OF THE INVENTION

Hydrocephalus is a condition associated with ventricular enlargement caused by a net accumulation of fluid in the ventricles. Non-communicating (or obstructive) hydrocephalus is hydrocephalus associated with an obstruction in the ventricular system and is generally characterized by increased cerebrospinal fluid (CSF) pressure. In contrast, communicating (or non-obstructive) hydrocephalus is a form of hydrocephalus which does not arise from a visible blockage in the flow of cerebrospinal fluid. Normal Pressure Hydrocephalus (NPH), a form of communicating hydrocephalus, is a clinical condition which principally affects the elderly. It is characterized by a triad of symptoms: Motor disturbances (mostly gait impairment), incontinence and dementia; associated with ventricular enlargement in the absence of elevate intracranial pressure. (Hakim et al. (1965). *J Neurol Sci* 2:307-327; Verees et al. Management of Normal Pressure Hydrocephalus. *American Family Physician* (2004). In summary, NPH presents as an enlargement of the ventricles with a normal CSF pressure. NPH is a known and unique clinical entity justifying its own differential diagnosis with other brain atrophies.

The brain is suspended in CSF within the cranial cavity. CSF formed in the ventricles eventually flows through the subarachnoid space and drains into the venous sinuses, including the superior sagittal sinus. An increase in CSF pressure over intraparenchymal venous pressure tends to increase the size of the ventricles, whereas an increase in venous pressure over CSF pressure tends to reduce ventricular size. The intracranial venous system is composed of intraparenchymal veins and capillaries, veins of the subarachnoid space and the venous sinuses. The venous capillaries collect fluid from the extracellular space and form larger and larger veins ultimately traversing the subarachnoid space. The veins of the subarachnoid space are characterized by relatively thin walls and the majority of these veins are submerged in CSF. Partly because of their thin, flexible walls, changes in CSF pressure in the subarachnoid space are transmitted to the veins which in turns results in a change in the lumenal cross-sectional area of the veins (Hakim, 1985. *The physics and physicopathology of the hydraulic complex of the central nervous system*. PhD Thesis, Massachusetts Institute of Technology). The change in the cross-sectional area of the veins then results in changed resistance of the parenchymal venous circulation before draining into the venous sinuses. In summary, changes in subarachnoid CSF pressure are transmitted to the parenchymal venous system. The difference between intraparenchymal venous pressure and CSF pressure must be maintained in order to protect the brain tissue from distortion or deformation. Hydrocephalus has therefore been described as the result of an increased pressure differential between CSF and the intracranial venous pressures (Hakim 1985). The brain is essentially subject to two opposing pressures: the intraparenchymal venous pressure and the CSF pressure. Provided that there is no difference between these two pressures, remains constant, the brain is not subjected to stress or distortion.

In summary, there is no gradient, e.g., when Pcsf=Pv, the ventricular size does not change. When the gradient is such that Pcsf>Pv, the ventricles increase in size. This happens in high pressure hydrocephalus where Pcsf increases due to an obstruction in the circulation of the fluid and Pv remains normal, (Pcsf>Pv). This also happens in NPH, in which Pcsf remains normal, but Pv decreases below normal also producing a gradient such that Pcsf>Pv.

NPH is usually treated by implanting a ventricular shunt that drains excess CSF from the ventricles. These shunts are generally comprised of a cerebral catheter inserted through the brain into the ventricle and a one-way valve system that drains fluid from the ventricle into a reservoir of the body, such as the jugular vein or the peritoneum (see, for example, U.S. Pat. No. 3,886,948). The shunt causes CSF to drain from the ventricles so long as the CSF pressure is greater than the operating pressure of the valve. Treatment of NPH using a ventricular shunt requires that the valve have a lower operating pressure than a normal CSF pressure so that the ventricle can decrease in size. Since the intraparenchymal venous pressure cannot be lowered below the pressure of the Superior Saggital Sinus, the venous pressure remains unchanged by the shunt. As the CSF pressure is decreased by the shunt, eventually, the venous pressure becomes greater than the CSF pressure and as a result, unless an adjustment is made, the ventricles will continue to decrease in size. Excess decrease in ventricular size is itself associated with several complications, including, for example, slit ventricles and subdural hematomas. Therefore, once the ventricle has reached a normal size, the CSF pressure must be restored to a normal level. Implantation of a ventricular shunt can often be a successful treatment for NPH, however, there are situations where the ventricles do not return to normal size after shunt implantation. In addition, surgical implantation is itself associated with serious risks such as over and under-drainage as well as infection (Jones et al. (2008). Cerebrospinal Fluid Research 5:19. Shprecher et. al.. (2009). Curr Neurol Neurosci Rep 8 (5): 371-376).

It would therefore be advantageous to develop improved methods of treating and diagnosing normal pressure hydrocephalus that can optionally be utilized in conjunction with current available treatments for NPH. It would additionally be useful to develop methods of treating and diagnosing disorders of the central nervous system.

SUMMARY OF THE INVENTION

The present invention is based on the discovery that disorders of the central nervous system are characterized by and at least partially caused by a decreased flexibility or compliance of the veins and/or arteries in the subarachnoid space. Therefore, in one embodiment, the invention is directed to a method of treating a patient suffering from a disorder of the central nervous system comprising administering to said patient a pharmacologic agent that increases the flexibility of the walls of the veins and/or arteries, or a combination thereof, in the subarachnoid space of the brain. In certain aspects, the pharmacologic agent inhibits collagen accumulation or degrades collagen deposition on the walls of the subarachnoid veins and/or arteries.

The invention also encompasses a method comprising administering to said patient a pharmacologic agent that increases the flexibility of the veins and/or the arteries, or a combination thereof, said method further comprising implantation of a shunt that decreases CSF pressure in the brain of said patient.

The invention additionally encompasses a method of treating a disorder of the central nervous system in a patient in need thereof comprising administering to said patient a pharmacologic agent that increases the flexibility of the veins and/or arteries, and further comprising increasing the intraparenchymal venous pressure. In some embodiments, the venous pressure is increased by introducing the patient to a hyperbaric environment while simultaneously venting the CSF to the exterior of the hyperbaric environment, for example, by venting CSF from the ventricles.

In yet another aspect, the invention is directed to a method of treating a patient suffering from a disorder of the central nervous system comprising introducing said patient into a hyperbaric environment. In some aspects, of the invention, the method further comprises implanting into the brain of said patient a shunt that decreases CSF pressure into the brain of said patient prior to introducing the patient to a hyperbaric environment while simultaneously venting the CSF to the exterior of the hyperbaric environment.

The invention also encompasses a method of diagnosing a patient with a disorder of the central nervous system comprising detecting the presence of collagen deposition on the walls of the veins and/or arteries in the subarachnoid space of the brain of said patient. In yet another embodiment, the invention is a method of diagnosing a patient with a disorder of the central nervous system comprising detecting the presence of collagen deposition on the walls of the vessels of the eye.

In a further embodiment, the invention is directed to a method of diagnosing a patient with a disorder of the central nervous system in a patient comprising collecting a sample of CSF from said patient and detecting the presence and/or level of the agent that induces collagen formation in the adventia of the subarachnoid veins and/or arteries, or detecting a marker of the agent.

In a further embodiment, the invention encompasses a method of treating a disorder of the central nervous system in a patient in need thereof comprising mechanically increasing the pulse amplitude in the cranial cavity of said patient, wherein the increase in pulse amplitude is sufficient to increase the flow of waste products from the brain tissue into the extracellular space and/or CSF.

The invention also encompasses a method for the treatment of a disorder of the central nervous system in a patient in need thereof, comprising diagnosing the patient as possessing a pre-disposition for decreased flexibility of the subarachnoid veins and/or arteries or a pre-disposition for a disorder of the central nervous system; and administering to the diagnosed patient a pharmacologic agent that increases the flexibility of the veins and/or arteries, or a combination thereof, in the subarachnoid space of the brain of said patient, wherein the pharmacologic agent is administered in an amount effective to inhibit the hardening of the subarachnoid veins and/or arteries. In some embodiments, the diagnosing step comprises a method of diagnosis described herein.

In yet a further aspect, the invention is directed to a method for the treatment of a disorder of the central nervous system in a patient in need thereof comprising increasing the pressure of at least a portion of the cranial cavity of said patient by providing a pressure actuator within the cranial cavity, wherein the method comprises activating the implanted pressure actuator; and varying the pressure within the enclosed cranial cavity in an amount effective to simulate healthy brain pulsation and/or in an amount effective to increase removal of waste products from the brain.

In certain aspects, the disorder of the central nervous system is NPH. In certain additional aspect, the disorder of the central nervous system is Alzheimer's disease. In other embodiments, the disorder of the central nervous system is a dementia.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a drawing showing a sagittal cross-section of the human head, cerebrospinal fluid (CSF) circulation, and various anatomical structures including the sagittal sinus, the arachnoid villi, the subarachnoid space, the medulla, the Foramen of Magendie, the cerebral aqueduct, the choroid plexus, the third and fourth ventricles, the Foramen of Lushka.

FIG. 5A illustrates the Normal Brain, with normal size ventricles and normal subarachnoid veins. FIG. 5B illustrates a brain with Normal Pressure Hydrocephalus, in which the ventricles are enlarged and the Subarachnoid Veins are hardened.

FIG. 8A is a photograph of a cross-sections of a normal brain with normal ventricles and FIG. 8B is a photograph of a hydrocephalic brain with enlarged ventricles.

In FIG. 11A, a tube that is flexible and responsive to compression is placed at the opening of a balloon filled with liquid. It is possible to maintain the internal pressure of the balloon by applying pressure to the flexible tube. In contrast, in FIG. 11B, a rigid tube is placed at the opening of a balloon filed with liquid. Because applying pressure on the tube does result in compression, the interior pressure of the balloon is not maintained and the liquid flows out of the balloon. The flexible tube is analogous to a healthy vein or artery, whereas the rigid tube is analogous to a hardened vein or artery.

In FIG. 12A, the pressure of the liquid entering the chamber is able to influence the tube attached to the sponge and the sponge does not deform. In FIG. 12B, the pressure of the liquid entering the chamber is not able to transmit the increased pressure to the tube and the liquid in the sponge escapes and the sponge compresses.

FIGS. 14A, 14B, and 14C show photographs of veins (as visualized under the microscope) from the brain of a healthy human patient (FIG. 14A), a patient with high pressure hydrocephalus (FIG. 14B) and a patient with normal pressure hydrocephalus (NPH) (FIG. 14C) under normal light (left column) and under polarized light (right column). The exterior of the veins of the NPH brain are illuminated under polarized light whereas the veins of the healthy brain and high pressure hydrocephalic brain do not show any change. The "illumination" or optical activity of the exterior layer of the veins from a brain with NPH is due to the accumulation of collagen on the adventitia (external layer) of the venous walls.

FIG. 16A shows the chamber at atmospheric pressure and the ventricles in the brain of the patient are enlarged. In FIG. 16B, the pressure inside the chamber has been increased above atmospheric pressure (Hyperbaric chamber) and the ventricles have reduced in size because the intraparenchymal venous pressure was increased above the intraventricular CSF pressure.

FIG. 18A illustrates the cranial cavity with enlarged ventricles inside a hyperbaric chamber, with the pressure inside the chamber being atmospheric pressure. The CSF is vented outside the chamber. In FIG. 18B, the pressure inside the chamber is increased above atmospheric pressure. As the pressure in the chamber is increased above atmospheric pressure, the venous pressure will increase but not the CSF pressure, since it is vented outside the chamber, to atmospheric pressure. This creates a gradient such that the venous pressure will be higher than the CSF pressure and the ventricles will reduce in size.

In FIG. 19A, when the subarachnoid venous system is normal, during systole, these veins become compressed and help maintain the "squeezing" mechanism of the brain tissue so that the waste products are expelled. In FIG. 19B, in which the subarachnoid venous system is abnormal and has become hardened, the veins do not become compressed during systole and therefore the squeezing mechanism is dampened and the waste products start accumulating in the brain tissue.

DETAILED DESCRIPTION OF THE INVENTION

Figure 2A:
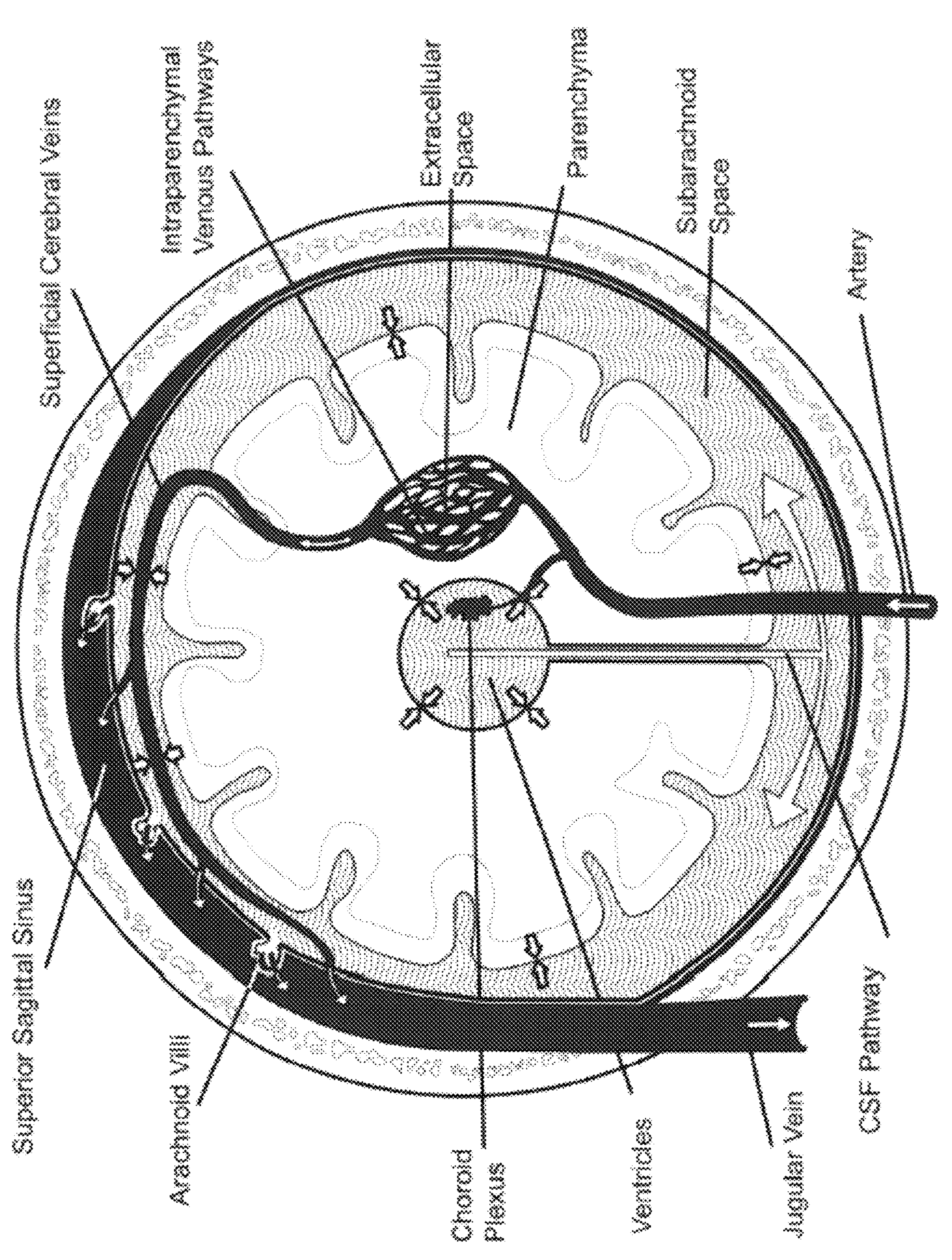
FIG. 2A is a drawing depicting a coronal cross-section of the cranial cavity and showing the pathway of the CSF from the ventricles into the Subarachnoid Space and finally draining into the Superior Sagittal Sinus. Also illustrated is the pathway of the Intraparenchymal Venous Blood through the Superficial Cerebral Veins into the Superior Sagittal Sinus.
Figure 2B:
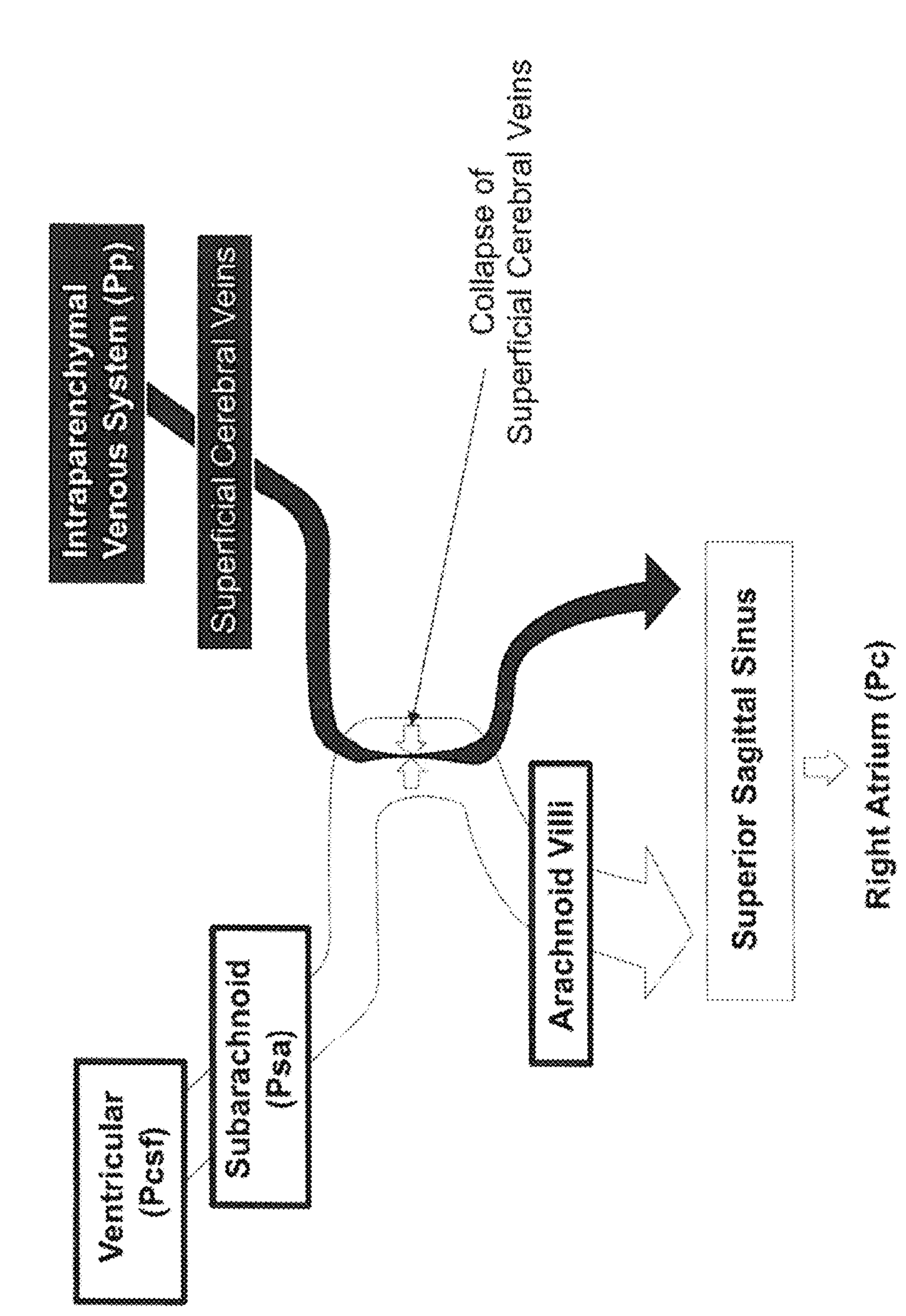
FIG. 2B is a schematic representation of the hydraulic mechanisms which keep the Ventricular Cerebrospinal Fluid Pressure (Pcsf) equal to the Intraparenchymal Venous Blood (Pp) and maintain the brain tissue under a dynamic equilibrium condition.
Figure 3:
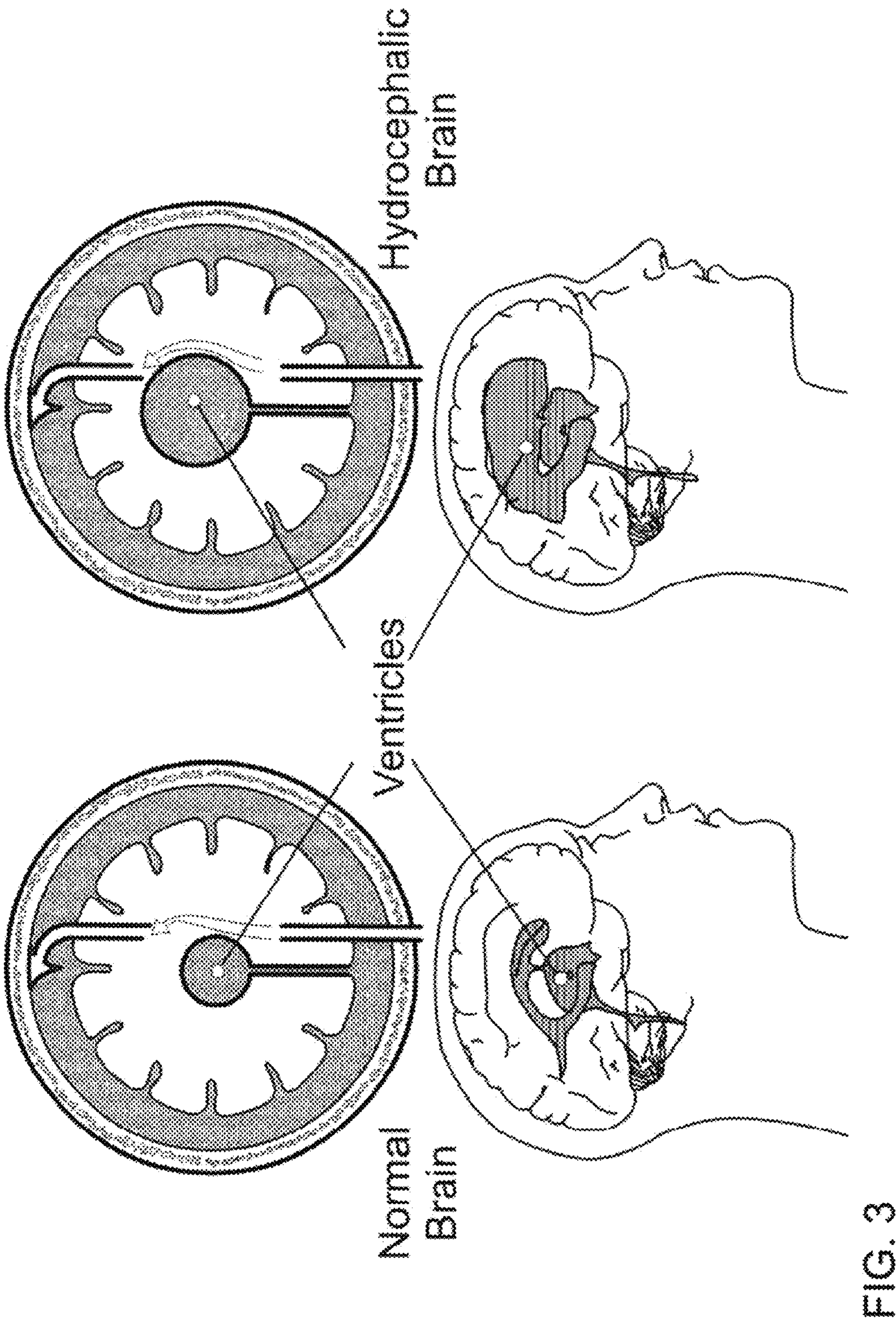
FIG. 3 is drawing comparing the size of the ventricles in a normal brain and in a hydrocephalic brain.
Figure 4:
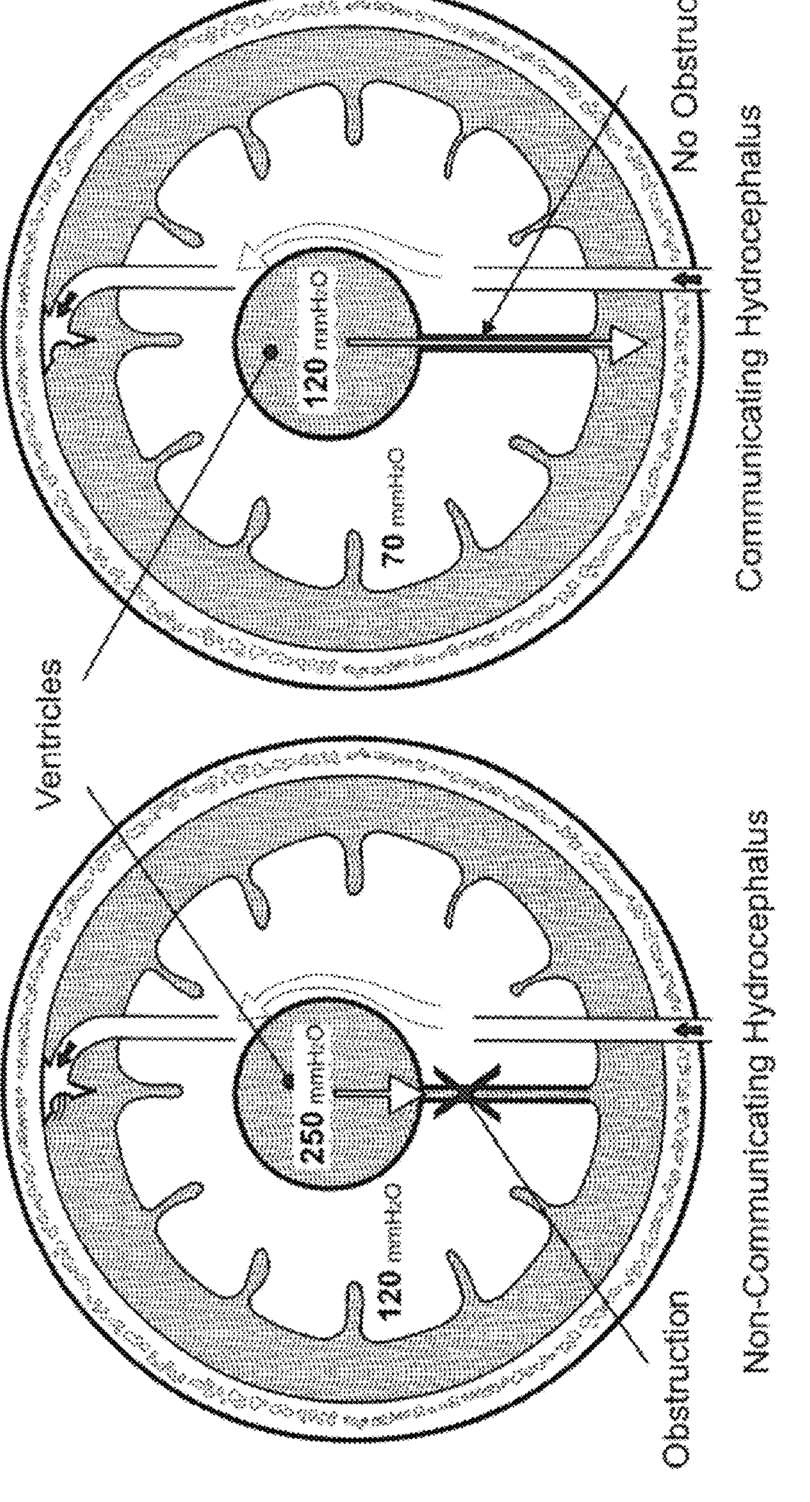
FIG. 4 is a drawing contrasting the pressures of the CSF in the ventricles and of the intraparenchymal veins of patients with high pressure hydrocephalus and patients with normal pressure hydrocephalus. Notice that in both types of hydrocephalus, the CSF Pressure is higher than the intraparenchymal venous pressure. In the case of High Pressure Hydrocephalus, Pcsf is high while Pv is normal. In the case of Normal Pressure hydrocephalus, Pcsf is normal while Pv is below normal.
Figures 5A, 5B:
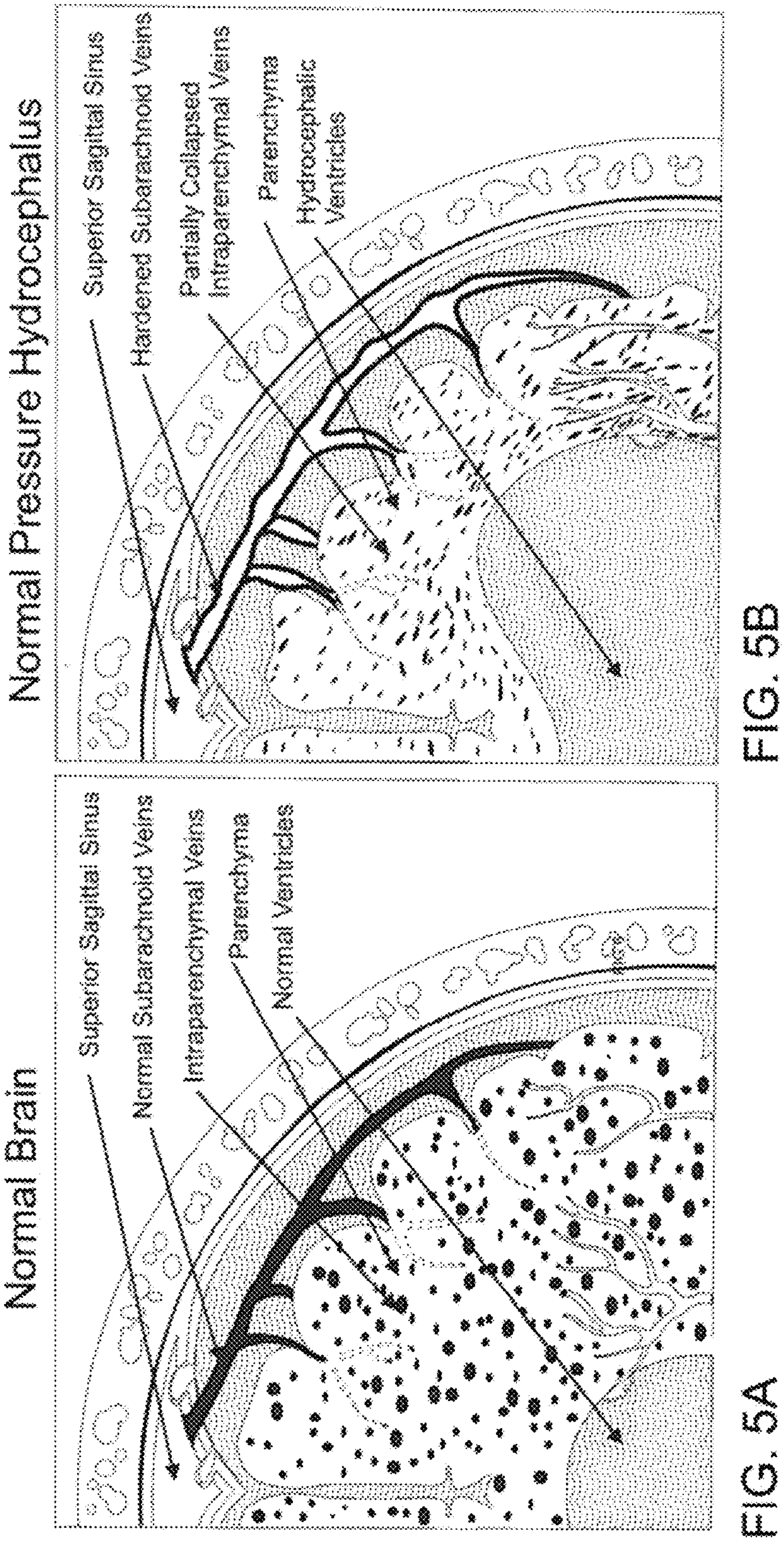
FIGS. 5A and 5B are drawings showing several anatomical structures in the brain including subarachnoid veins, intraparenchymal veins, sagittal sinus, parenchyma and ventricles.
Figure 6:
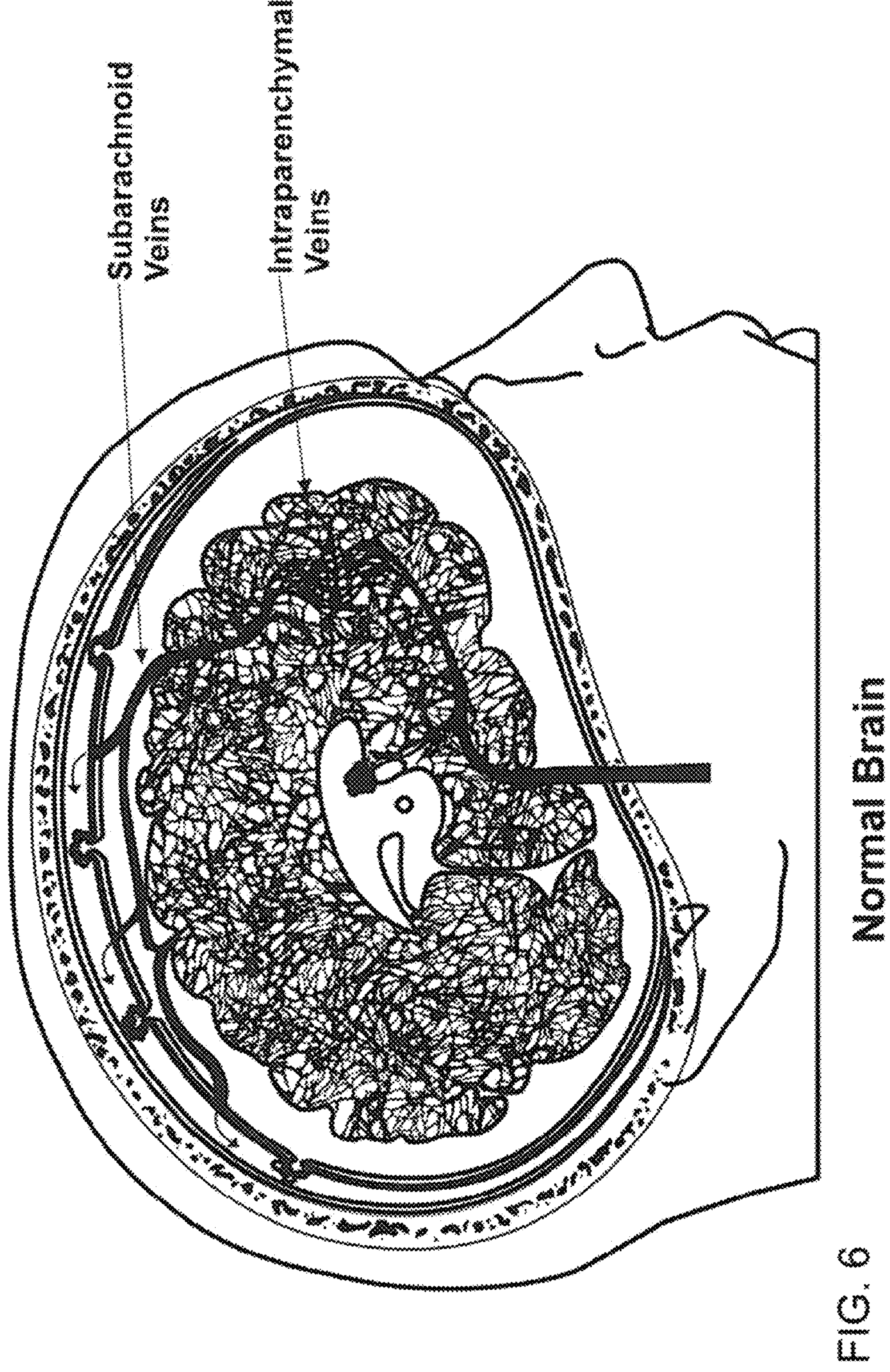
FIG. 6 is a drawing showing the cross-section of a normal brain where the subarachnoid veins and intraparenchymal veins are indicated. Ventricular size is normal and the veins are normal.
Figure 7:
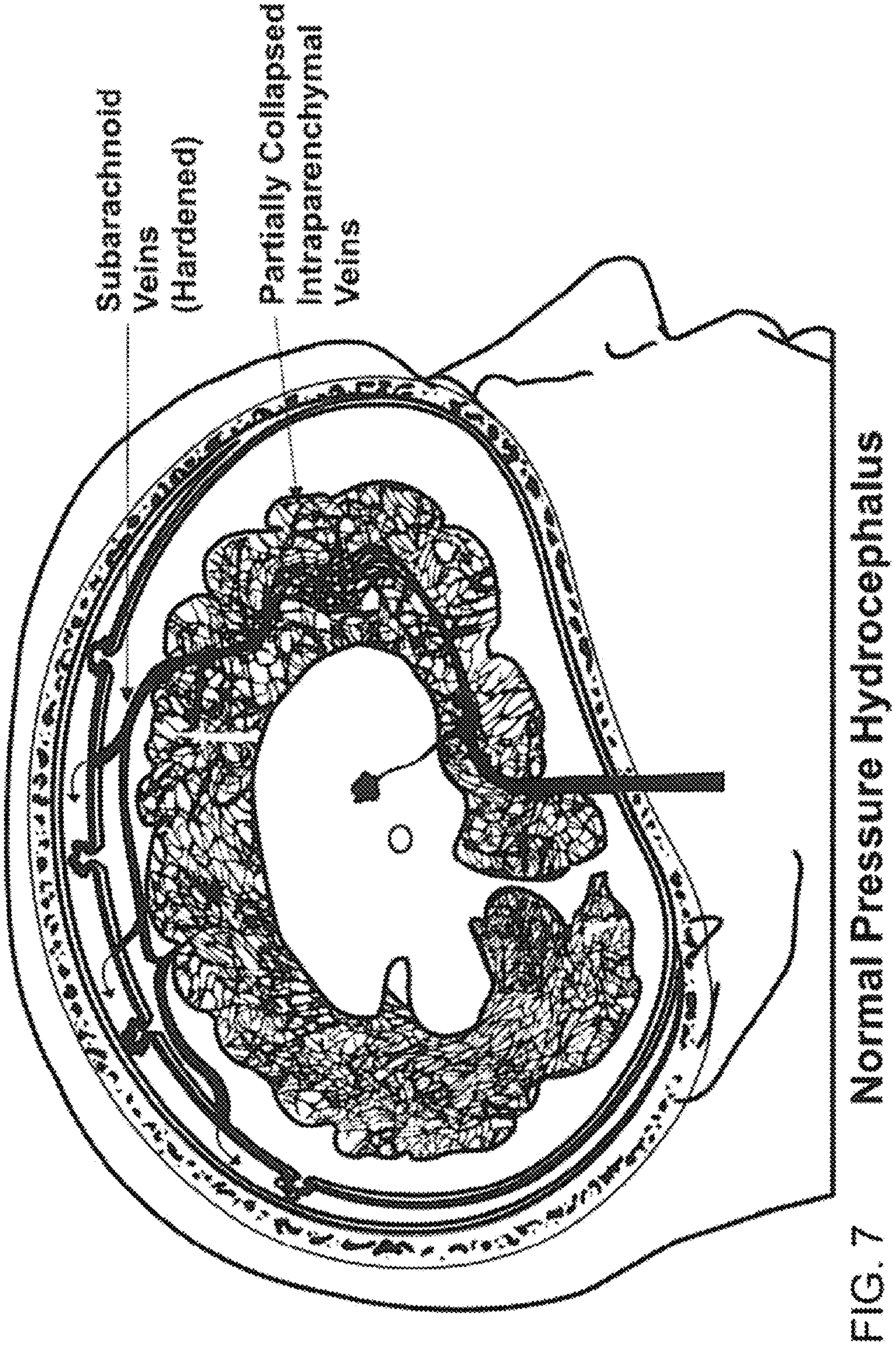
FIG. 7 is a drawing depicting the hardened subarachnoid veins, the partially collapsed intraparenchymal veins and the enlarged ventricles of a patient with Normal Pressure Hydrocephalus.

A description of preferred embodiments of the invention follows.

As discussed above, the present invention is based on the discovery that disorders of the central nervous system are at least partially caused by an imbalance between CSF pressure and the intraparenchymal venous pressure. With respect to hydrocephalus, high pressure hydrocephalus is normally produced by an obstruction in the pathways of the CSF which leads to an increase in CSF pressure. This increase in CSF pressure makes the CSF pressure greater than the intraparenchymal venous pressure resulting in an enlargement of the ventricles and an abnormal accumulation of CSF or hydrocephalus. In contrast, NPH is produced by a decrease in the intraparenchymal venous pressure (while CSF pressure remains normal) which also results in an enlargement of the ventricles and an accumulation of CSF, or hydrocephalus. It has been discovered that in the pathology samples of brains from patients with NPH, the blood vessels in the subarachnoid space of the brain exhibit a marked increase in the formation/accumulation of collagen in the adventitia or external layer of the blood vessels. It is believed that when the walls of the veins become hardened by collagen formation on their exterior, the CSF pressure can no longer be transmitted through the walls of the veins. Thus, the intraparenchymal venous pressure decreases in value below the pressure of the CSF, resulting in a pressure gradient such that the CSF pressure will be greater than the intraparenchymal venous pressure. This results in an increase in ventricular size (hydrocephalus) and the accumulation of CSF which characterizes NPH.

Although not wishing to be bound by theory, it is hypothesized that waste products produced by the brain are normally eliminated by pulsation of the brain within the rigid cranial cavity. During systole, when the arterial pressure increases, the brain tissue is compressed which pushes the waste products into the extraparenchymal fluid and into the CSF. Once in the CSF, the waste products are carried away into the bloodstream. As will be appreciated, in order for waste products to be removed by compression of the brain tissue, the veins in the subarachnoid space must be flexible and able to partially collapse during systole. When the veins have decreased flexibility, e.g., by the accumulation of collagen, the cleaning mechanism is dampened and as a result, only a portion of the waste products that are normally removed will be eliminated. The waste products then accumulate, producing damage to the neurons, for example, eventually leading to a disorder of the central nervous system, such as Alzheimer's disease. Therefore, it is believed that the hardening of the walls of the blood vessels in the subarachnoid space, in particular, those of the veins, contributes to disorders of the central nervous system.

With respect to NPH and Alzheimer's disease, it is believed that one difference between this process in NPH and Alzheimer's disease is the time over which the damage occurs. The hardening of the veins of NPH occurs in a relatively short period of time whereas the hardening of the veins in Alzheimer's disease occurs over a longer period of time. In NPH, the hardening of the veins takes place over days or a few weeks, and results in the enlargement of the ventricles and the symptoms associated with this enlargement. This enlargement of the ventricles is reversible and thus, NPH can be treated. In the case of Alzheimer's disease, the hardening of the veins is believed to occur over a longer period of time, for example, over years, and the damage, having occurred over years, is not reversible.

The present invention is based on the disorders of the central nervous system are characterized by decreased flexibility or compliance of veins and/or arteries in the subarachnoid space (also referred to herein as subarachnoid veins and subarachnoid arteries). This decreased flexibility of the subarachnoid veins and/or arteries means that that changes in CSF pressure are not transmitted to the veins and the lumenal cross-sectional area of the veins and arteries does not change in response to CSF pressure.

As discussed above, in the normal brain, changes in CSF pressure in the subarachnoid space essentially compress the veins which in turns results in a change in the lumenal cross-sectional area of the veins. Because the veins in the subarachnoid space are thin-walled and flexible, the veins are able to respond to an increase in CSF pressure by decreasing their lumenal cross-sectional area. Thus, the pressure difference between CSF pressure and venous pressure remains in equilibrium and the ventricles remain in their normal state. In contrast, in the brain of a patient with a central nervous system disorder such as normal pressure hydrocephalus (NPH) or Alzheimer's disease, the walls of the veins are characterized by decreased flexibility. In NPH, because the pressure of the venous system does not increase in response to an increase in CSF pressure, the differential between the CSF pressure and venous pressure increases and the ventricles increase in size. In Alzheimer's disease and other disorders of the central nervous system, because the walls of the subarachnoid veins have decreased flexibility, waste products that are normally expelled into the CSF accumulate and damage the neurons.

In addition, it is believed that the accumulation of collagen on the arteries is another contributing factor in disorders of the central nervous system. For example, we have observed that the arteries in the subarachnoid space in patients with NPH have an accumulation of collagen in the adventitia. In the case of Alzheimer's, it is believed that the hardening of the arteries may also dampen the cleansing and compression mechanism described above.

As used herein, the words "a" or "an" are meant to encompass one or more, unless otherwise specified.

A "patient" is a human subject in need of treatment.

It is to be understood that disorders of the central nervous system include, for example, NPH, Alzheimer's disease and conditions associated with dementia. Conditions associated with dementia include Alzheimer's disease, and dementia associated with Lewy body disease, frontotemporal lobar degeneration, cerebrovascular disease, dementia associated with traumatic brain injury, Parkinson's dementia, Creutzfeldt-Jakob disease, and alcoholic/toxic dementia.

As used herein, the term "inhibiting" or "decreasing" or "reducing" encompasses causing a net decrease by either direct or indirect means. The term "increasing" or "raising" means to cause a net gain by either direct or indirect means.

The term "agent" is used herein to denote a chemical compound, a mixture of chemical compounds, a biological macromolecule (including, for example, a nucleic acid, an antibody, a protein or portion thereof, e.g., a peptide), a naturally occurring chemical compound or biologic macromolecule, or an extract made from biological materials such as bacteria, plants, fungi, or animal (particularly mammalian) cells or tissues.

"Treating" or "treatment" includes the administration of the compositions, compounds or agents of described herein to prevent or delay the onset of the symptoms, complications, or biochemical indicia of a disease, alleviating or ameliorating the symptoms or arresting or inhibiting further development of the disease, condition, or disorder.

A "therapeutically effective amount" or an "effective amount" is an amount which, alone or in combination with one or more other active agents, can control, decrease, inhibit, ameliorate, prevent or otherwise affect one or more symptoms of a disease or condition to be treated and/or achieves a specifically recited objective.

The method of treatment described herein which comprises administration of a pharmacologic agent that increases the flexibility of the subarachnoid veins and/or arteries is useful for the treatment of disorders of the central nervous system. In some embodiments, the patient is suffering from NPH. In other embodiments, the patient is suffering from Alzheimer's disease. In some embodiments, the patient is treated as described herein at an early stage of Alzhiemer's disease, for example when the Alzheimer's disease is diagnosed or detected at an early stage and the methods described herein can halt or inhibit the formation of collagen on the adventitia of the blood vessels. In yet other embodiments, the patient is suffering from dementia. Neurologists are familiar with the symptoms and diagnosis of dementia, NPH, Alzheimer's disease and an early stage of Alzheimer's disease. In certain aspects of the invention, an effective amount of a pharmacologic agent that increases the flexibility of the subarachnoid veins is administered to a patient suffering from a disorder of the central nervous system. In yet additional aspects of the invention, an effective amount of a pharmacologic agent that increases the flexibility of the subarachnoid arteries is administered to a patient suffering from a disorder of the central nervous system. It is to be understood that the agent that increases the flexibility of the subarachanoid veins and/or arteries can also be referred to herein as an agent that reduces the fibrosis of the subarachnoid veins and/or arteries as an agent that reduces the stiffening of the veins and/or or arteries. In some embodiments, the agent increases the flexibility of the subarachnoid veins. In additional embodiment, the agent increases the flexibility of the subarachnoid arteries. In yet other embodiments, the agent increases the flexibility of the subarachnoid veins and/or arteries. The flexibility of the subarachnoid veins and/or arteries is increased after administration of a pharmacologic agent when the vein and/or artery has greater flexibility than that before administration of the agent to the patient. In some aspects, the flexibility of the veins and/or arteries is increased when there is change in the luminal cross-sectional of the veins and/or arteries in response to CSF pressure compared to the change in the luminal cross-sectional area in response to the same CSF pressure before administration of the pharmacologic agent.

In certain aspects of the invention, the pharmacologic agent is an anti-fibrotic agent. Anti-fibrotic agents have been described extensively in the literature and include, for example, aprotinin, aprotinin derivatives, C1-esterase inhibitors, ε-amino-n-caproic acid (EACA), α-2 -macroglobulin, α-2-plasmin inhibitor, α-1-plasmin inhibitor, plasminogen activator inhibitor, inhibitor or inactivator of activated protein C, a plasmin-binding substance, tranexamic acid, cis-hydroxyproline (cHYP), interferon, hepatocyte growth factor, TGFβ1 inhibitors, TGFβ2 inhibitors and PDGF inhibitors. Inhibitors of TGFβ1, TGFβ2 and PDGF include, for example, antibodies, soluble proteins, binding proteins that directly or indirectly inhibit the binding of these proteins to their receptors by either binding to the growth factor itself, antisense oligonucleotides, RNAi or ribozymes which act to inhibits the expression of these proteins.

Figures 9A, 9B:
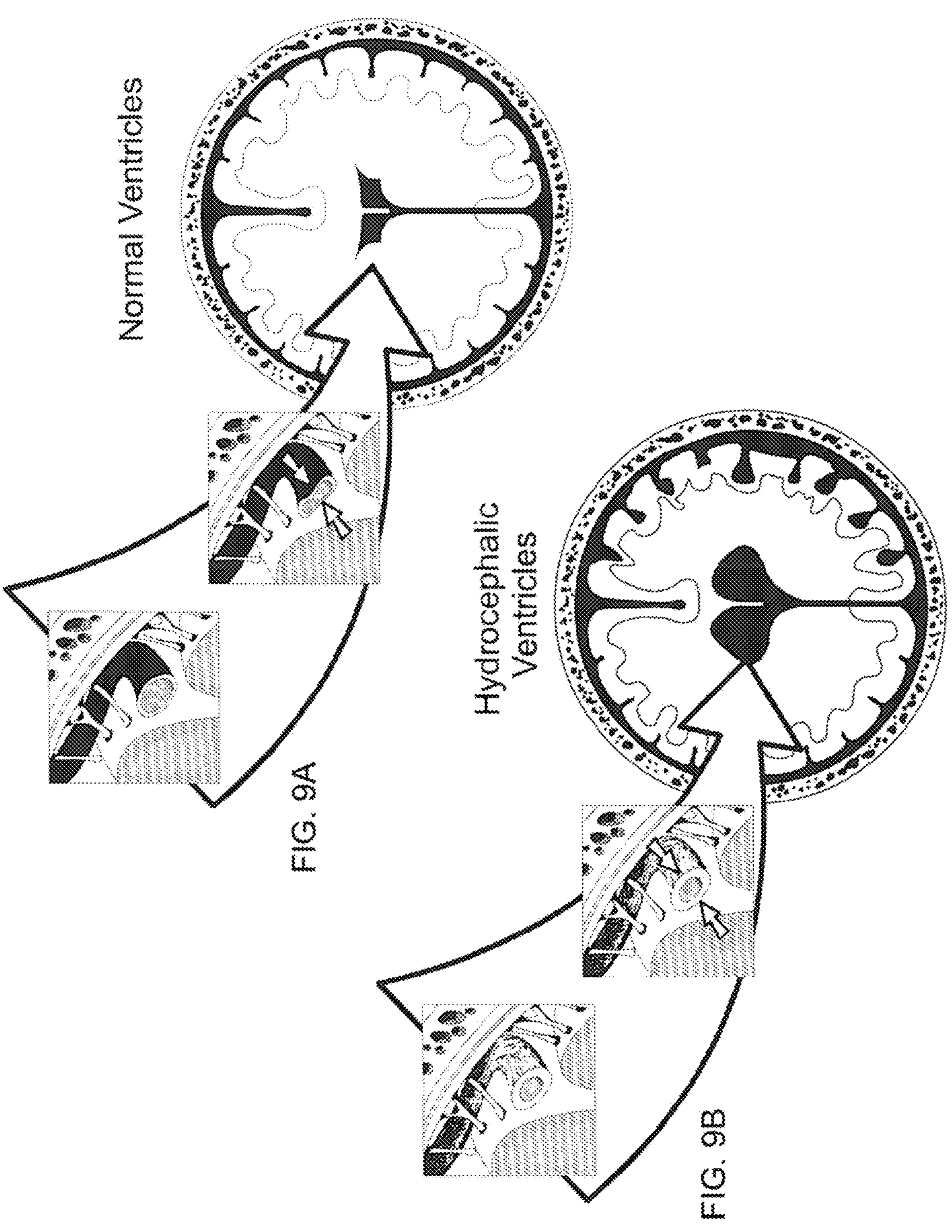
FIG. 9A is a series of drawings showing the normal state of subarachnoid veins: i) in the normal state, the veins are flexible and thin-walled, ii) the circulation of CSF is normal, iii) the veins respond to the pressure of the CSF by collapsing, iv) the pressure of the CSF and the parenchymal venous pressure are at equilibrium and v) the ventricles remain normal size.
FIG. 9B is a series of drawings showing the state of veins in the brain of a patient with NPH: i) the veins have lost their flexibility and have stiffened walls, ii) the circulation of the CSF remains normal, iii) the veins are unable to collapse in response to pressure of the CSF, iv) the parenchymal venous pressure becomes lower than the pressure of the CSF, and v) the ventricles increase in size.
Figure 10:
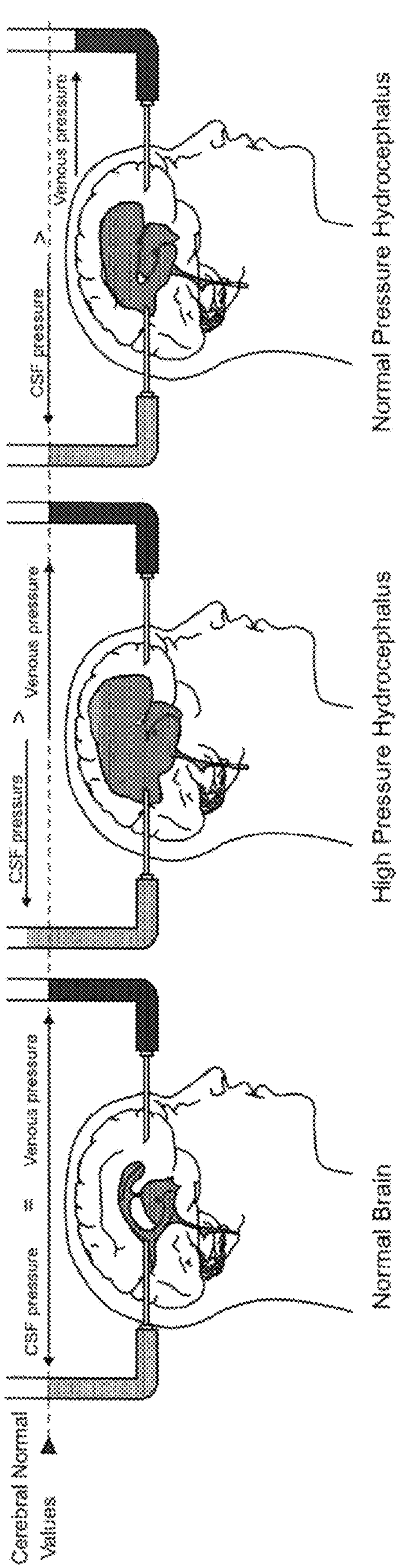
FIG. 10 illustrates three different states of the brain. In the Normal Brain, the CSF Pressure and the Venous Pressure are equal. In the brain with High Pressure Hydrocephalus, the ventricles are enlarged, the CSF pressure is increased and the venous pressure is normal. In the brain with Normal Pressure Hydrocephalus, the ventricles are enlarged, the CSF pressure is normal and the venous pressure is below normal.
Figures 11A, 11B:
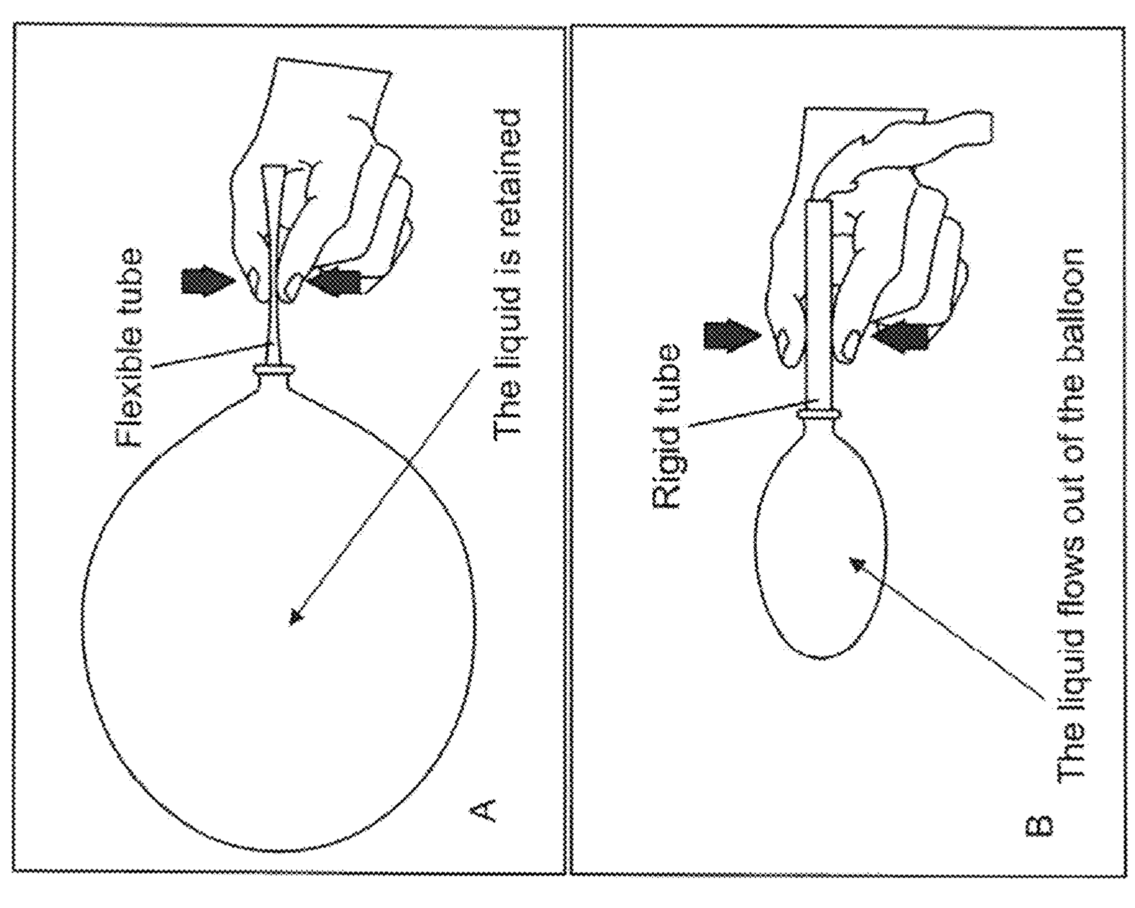
FIGS. 11A and 11B are drawings of a simple model demonstrating the importance of flexibility in the subarachnoid veins.
Figures 12A, 12B:
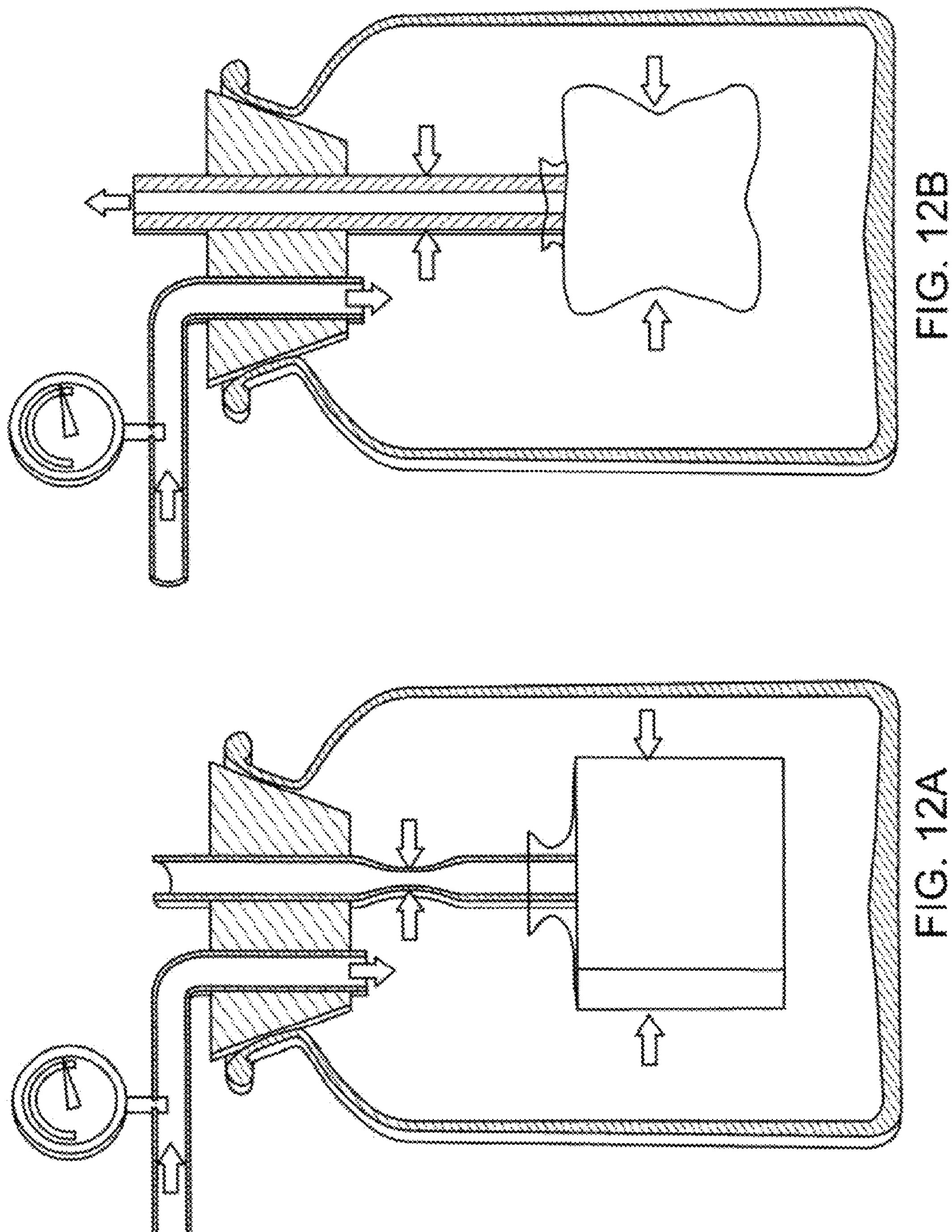
FIGS. 12A and 12B are drawings of another model demonstrating the importance of maintaining flexibility of the subarachnoid veins. The model shows a system comprising a closed chamber housing a sponge; the sponge is attached to a tube which is open to the outside of the chamber. The chamber also includes a path for liquid to be injected into the chamber, which path is attached to a manometer that measures the pressure of the liquid entering the chamber. The only difference between FIGS. 12A and 12B is that tube in FIG. 12A is flexible whereas the tube in FIG. 12B is rigid.
Figure 13:
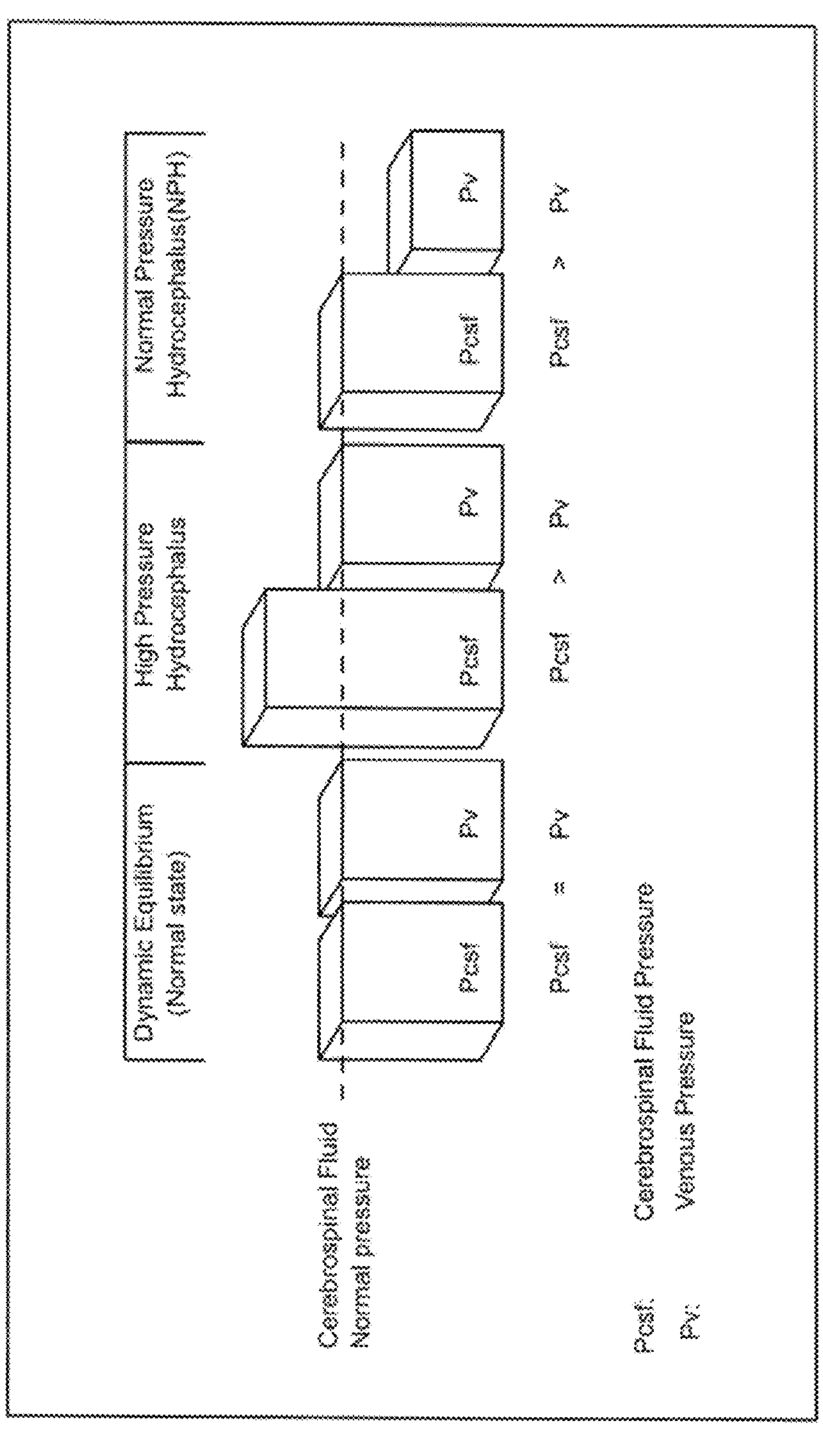
FIG. 13 is a bar graph comparing the pressure of the cerebrospinal fluid and the venous pressure in the normal brain, in the brain of a patient with high pressure hydrocephalus and in the brain of a patient with normal pressure hydrocephalus.
Figure 15:
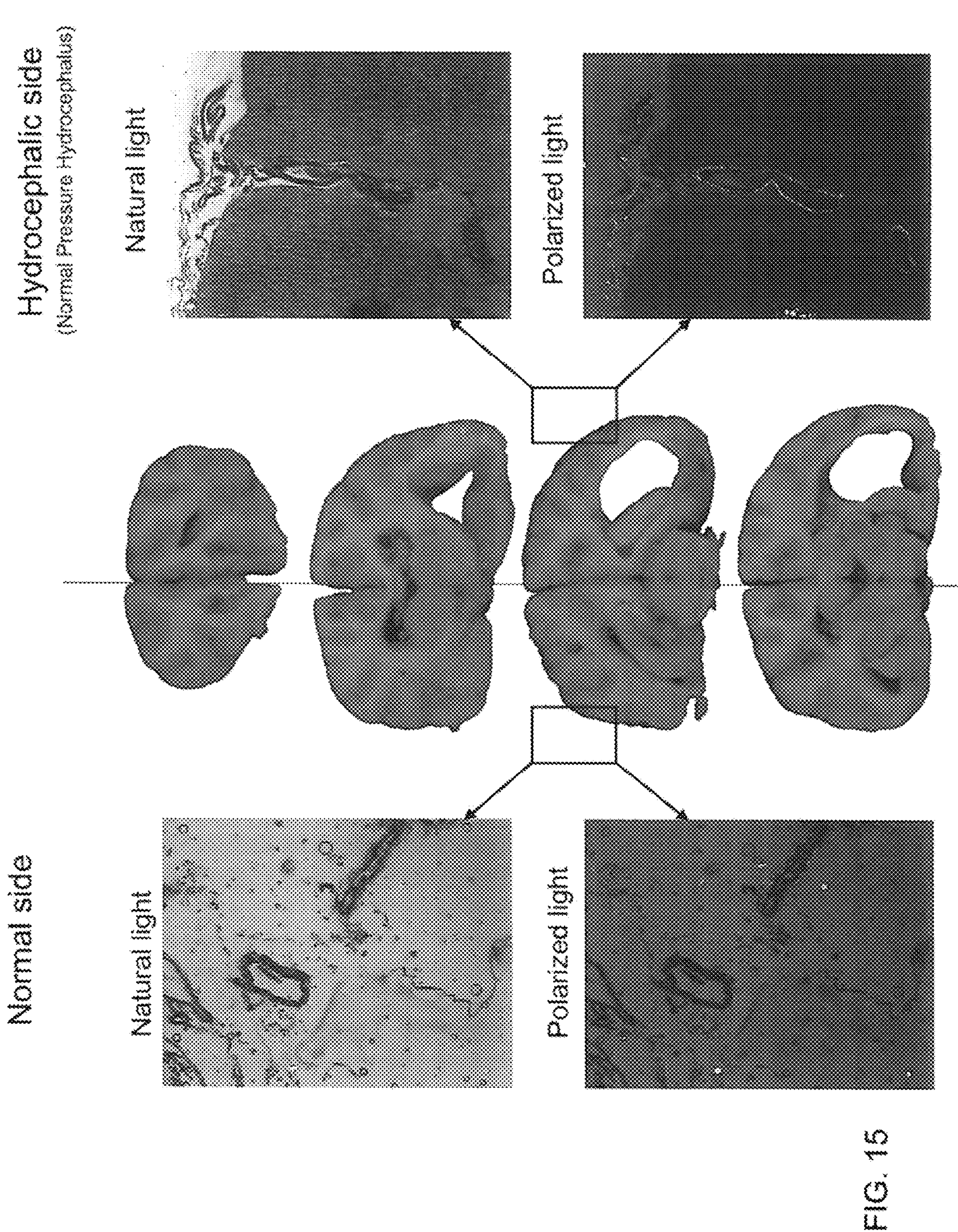
FIG. 15 shows photographs of coronal cross-sections of a canine brain which developed Normal Pressure Hydrocephalus unilaterally. The left side or normal side illustrates a cross section through brain tissue including a vein from the surface, as seen under the microscope using normal light (top) and polarized light (bottom). The right side or hydrocephalic side illustrates a cross-section through brain tissue including a vein from the surface, as seen under the microscope using normal light (top) and polarized light (bottom). Under polarized light, only the vein from the hydrocephalic side has hardened and shows optical activity (illumination) due to the accumulation of collagen on the adventitia.
Figures 16A, 16B:
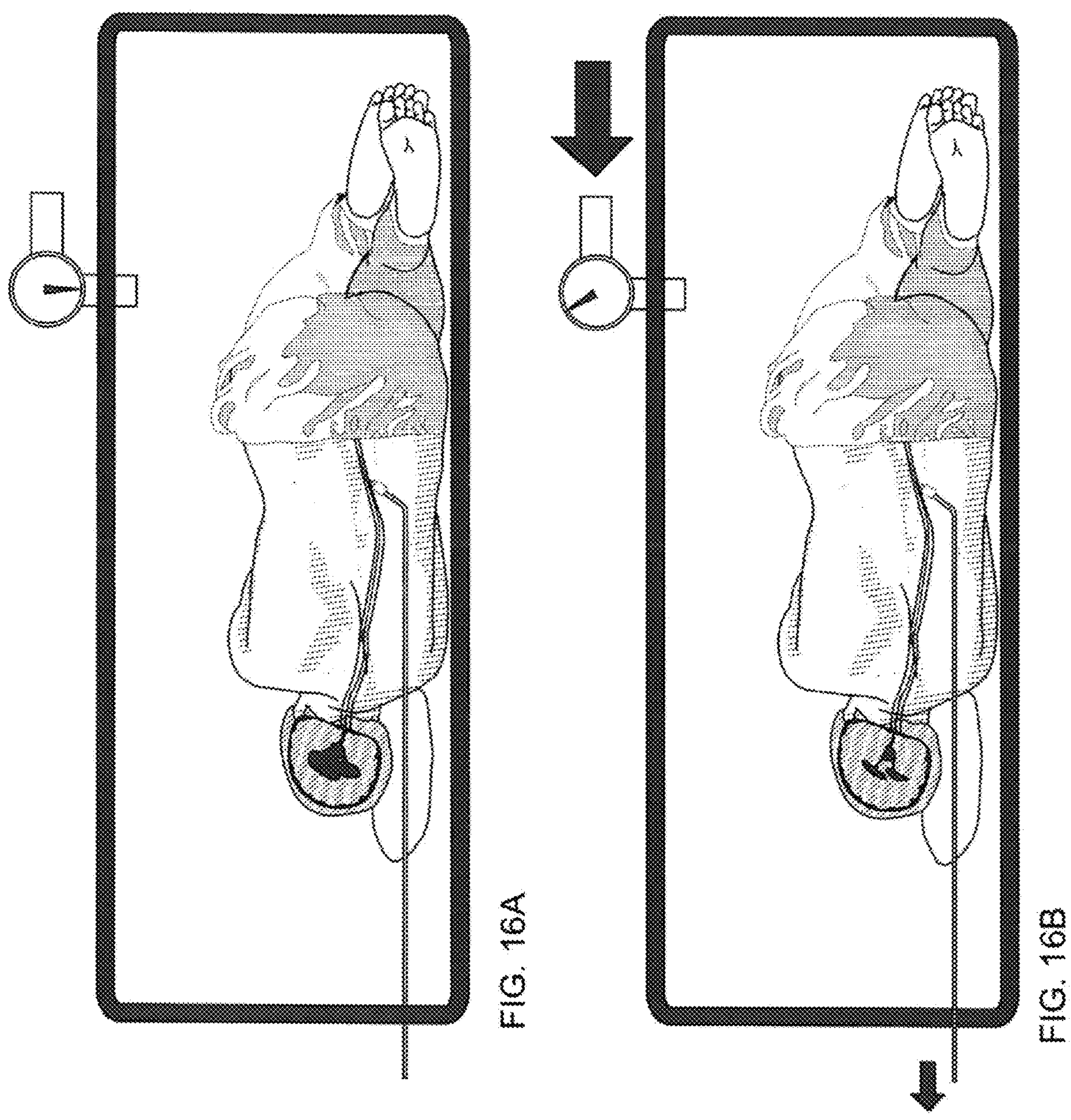
FIGS. 16A and 16B illustrate a patient inside a variable altitude chamber with a catheter venting the CSF at the spine (Spinal Tap) to the outside of the chamber.
Figures 17A, 17B:
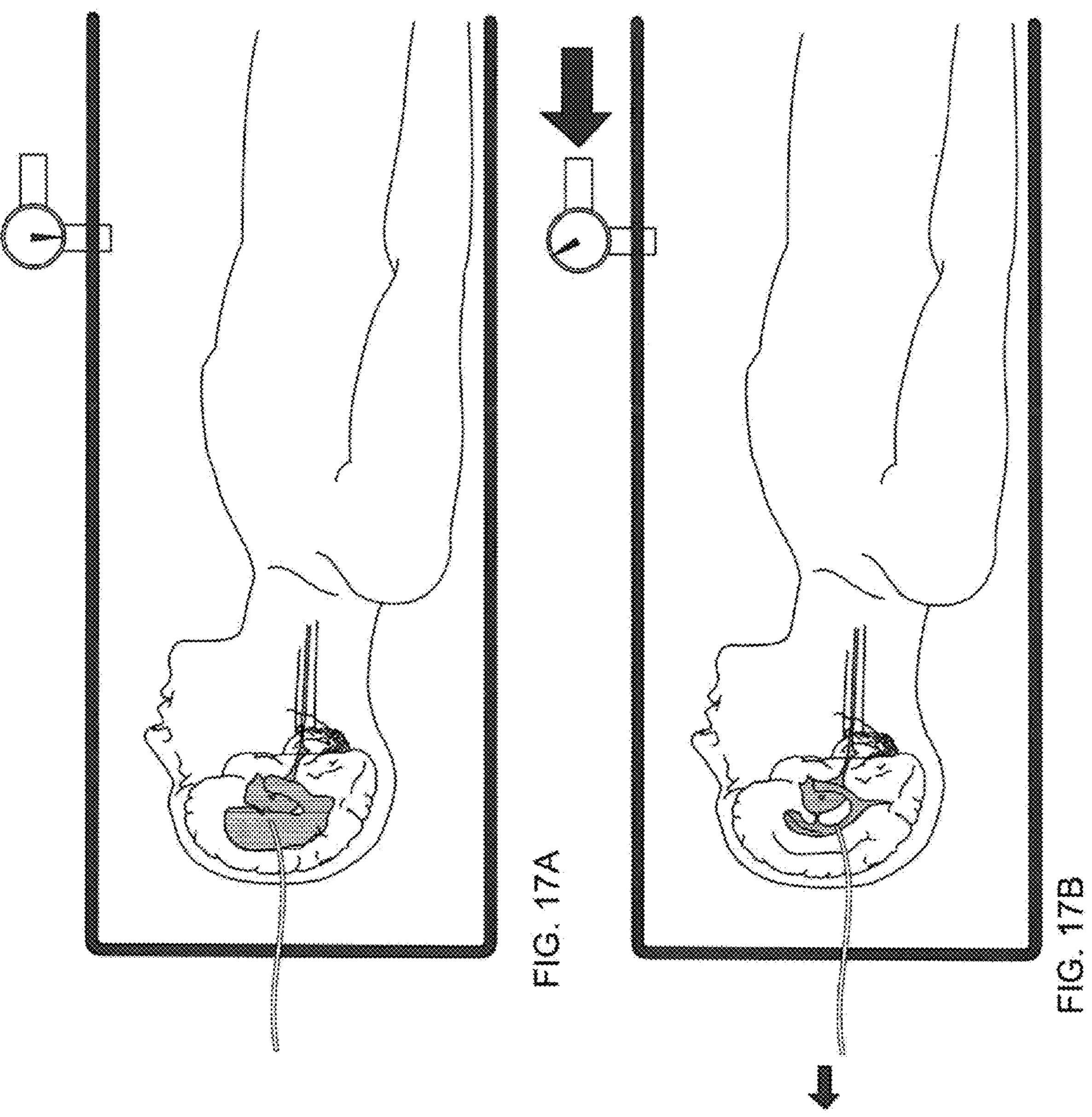
FIGS. 17A and 17B illustrate the same examples as those in FIGS. 16A and 16B, the only difference being that the CSF is vented directly from the ventricles to the outside of the chamber.
Figure 18A:
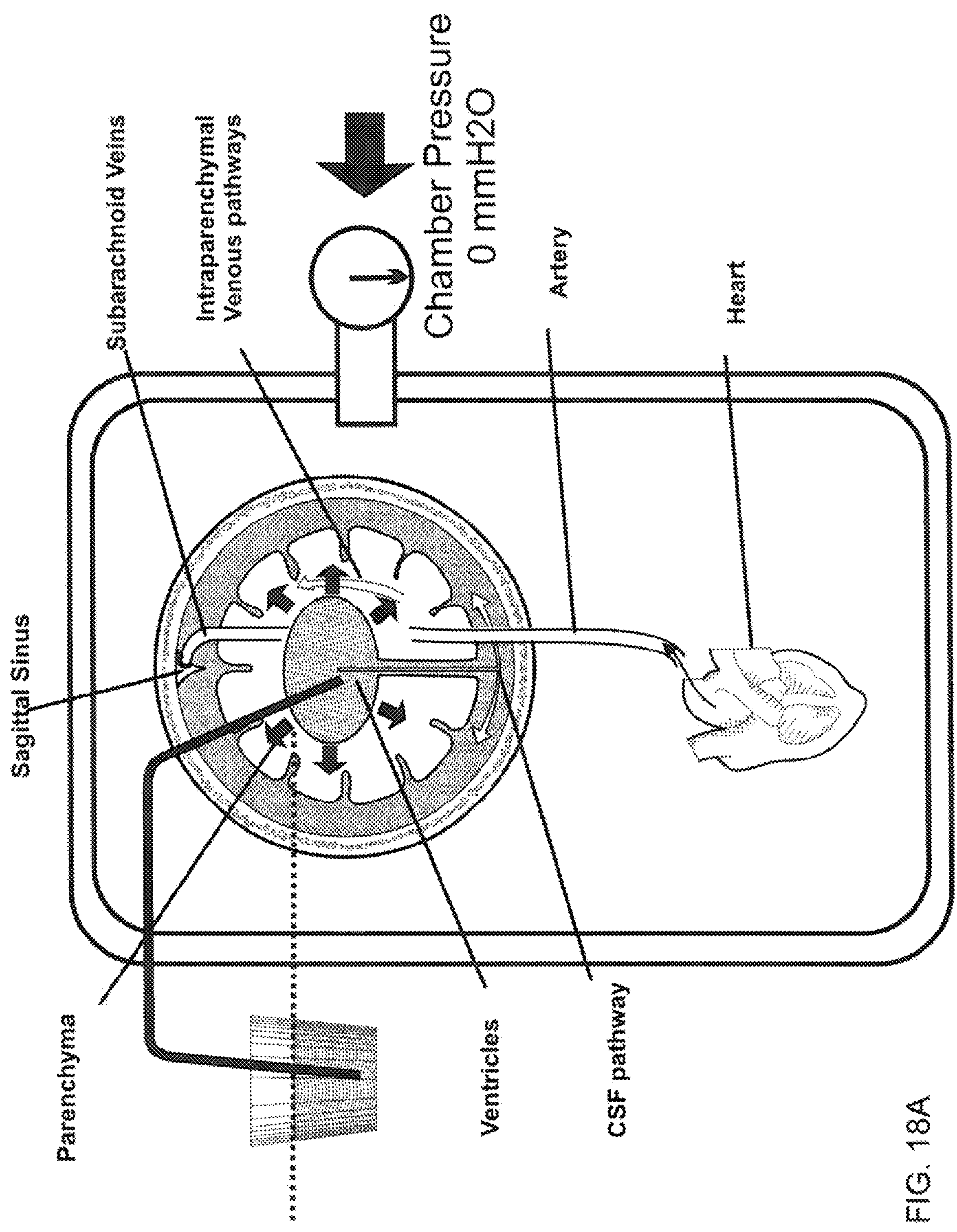
FIGS. 18A and 18B illustrate the same concept as that of FIGS. 16A, 16B, 17A, and 17B.
Figure 18B:
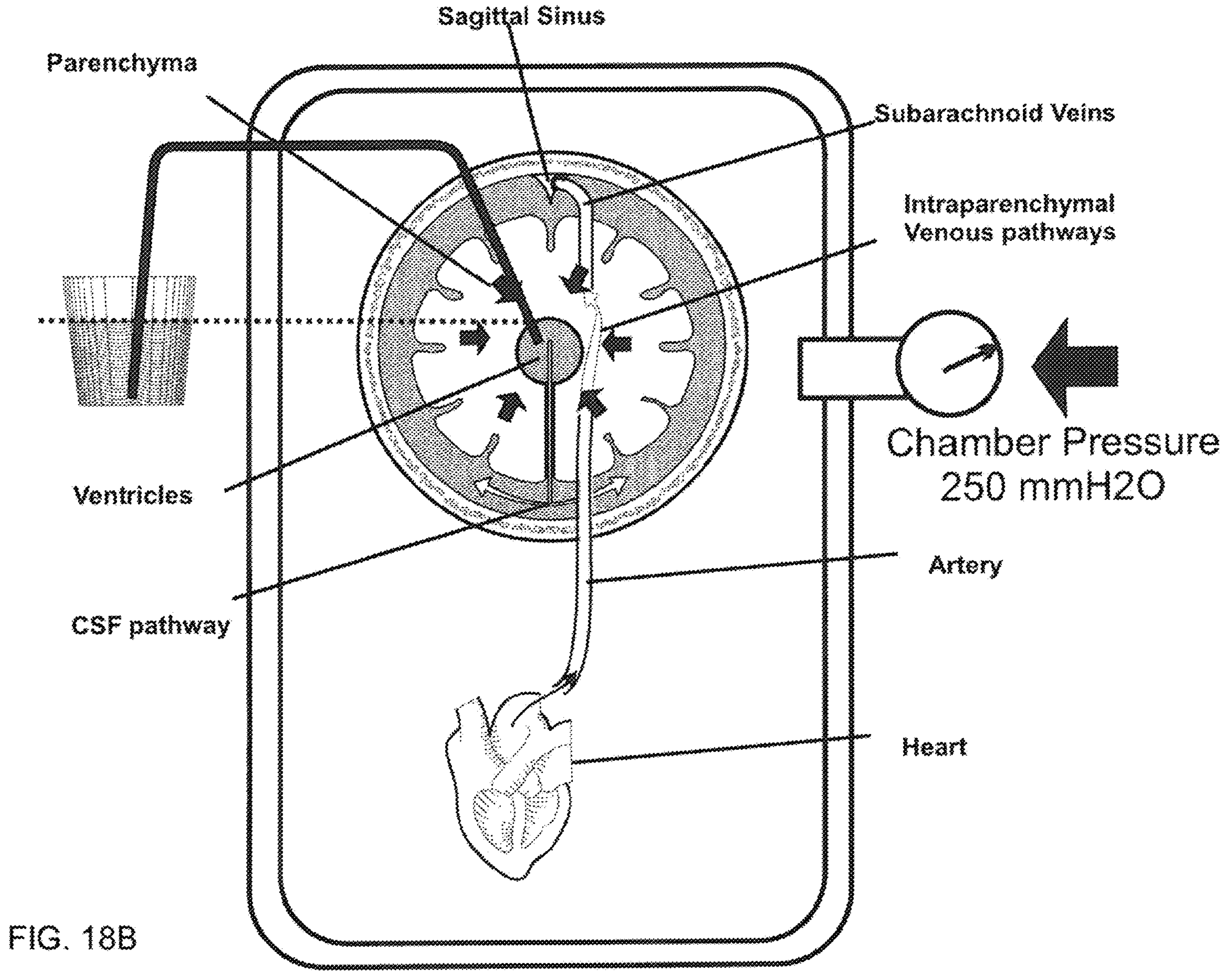
Figures 19A, 19B:
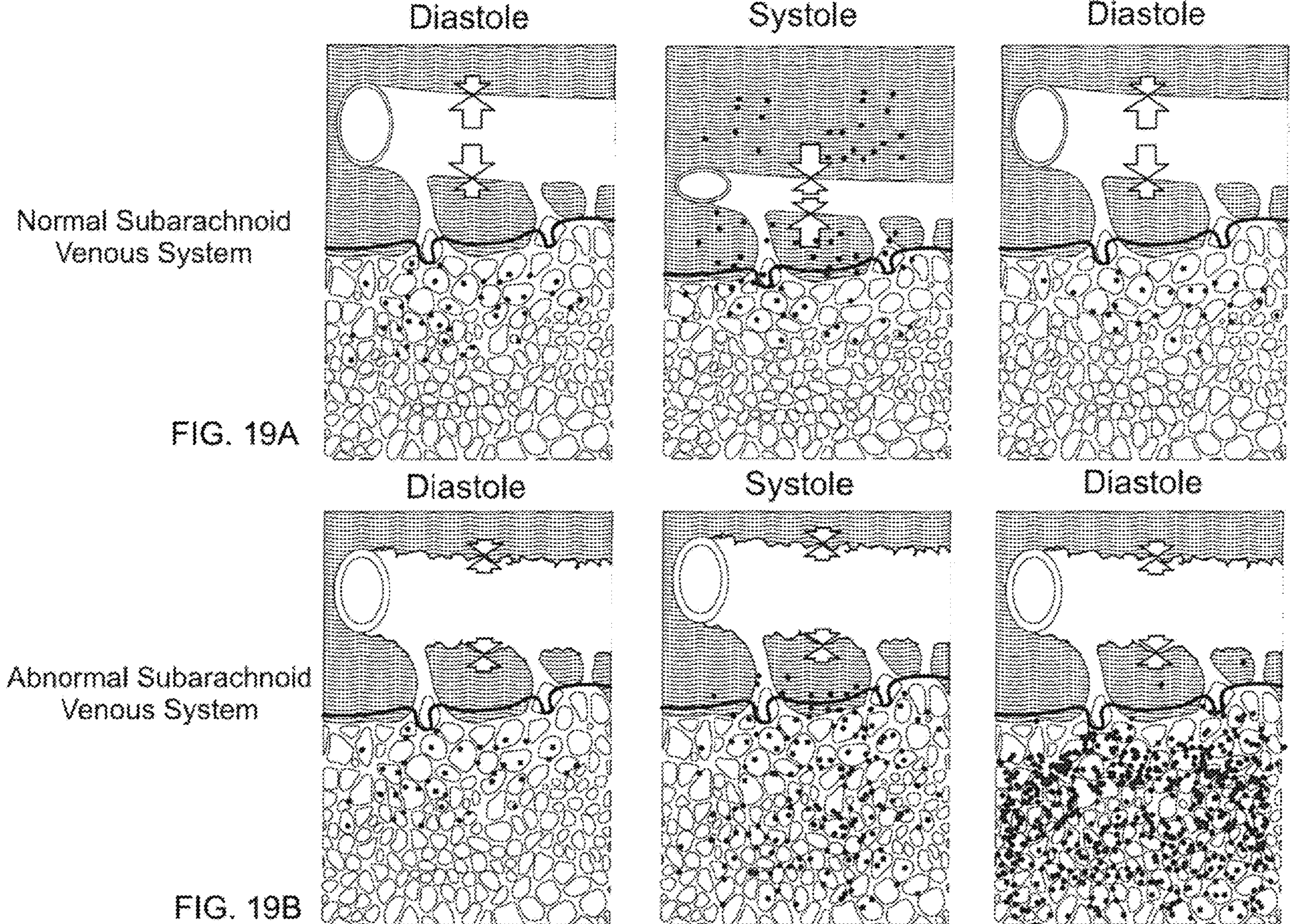
FIGS. 19A AND 19B illustrate the pumping mechanism that occurs with the pulsation of the brain and helps move the waste products from inside the brain to outside of the brain traveling through the extracellular spaces and CSF. This mechanism would be similar to having a sponge which is full of ink and submerging it in water and slowly compressing and releasing it, in such a way that eventually the ink would be cleared out from the sponge and into the water.

As shown in FIGS. 9 and 14, the decreased flexibility of the subarachnoid veins can be at least partially attributed to the accumulation of collagen fibrils on the exterior of the wall of the veins. Therefore, in some aspects of the invention, the pharmacologic agent is an agent that inhibits collagen accumulation or degrades collagen. Agents that inhibit collagen accumulation and/or degrade collagen include, for example, agents that inhibit collagen synthesis, agents that enhance collagen degradation, agents that inhibit formation of collagen fibrils and/or agents that inhibit folding of the protein. Such agents include, for example, anti-collagen antibodies, collagenase enzymes, phorbol 12-myristate 13-acetate (Goldstein et al. (1990). JBC 265: 13623-8), cis-4-hydroxyproline and derivatives thereof, proline and derivatives thereof, L-azetidine-2-carboxylic acid and derivative thereof, tranexamic acid, TNF-a (Pischon et al. (2004). JBC 279:30060-5 and prolyl-4-hydroxylase inhibitors (Nwogu et al. (2001). Circulation 104:2216-21).

The pharmacologic agent can be administered in any suitable manner that allows the agent to exert its effects in the brain. In some aspects of the invention, the agent is administered directly or indirectly into the cerebrospinal fluid. Systemic and intracerebral routes have been reported for the purpose of delivering drugs to the CSF. A consideration in intravascular administration is of course penetration through the blood brain barrier, especially for polar or hydrophilic agents. However, a number of techniques for systemic delivery of drugs into the CSF and brain have been described, for example, encapsulation of drugs in to liposomes and the use of nanomedicines have been described (Merkus et al. (2002). Br. J. Clin. Pharmacol. 54 (5): 560 and Nowacek et al. (2009). Nanomedicine 4 (5): 557-74). In yet another aspect, the agent is administered intrathecally or intracerebroventricularly.

The pharmacologic agent can be selected from the group consisting of a small molecule, an antibody, a peptide and a nucleic acid. As used herein, the term "peptide" includes proteins and antibodies as well as molecules comprised of two or more amino acids. Antibodies include polyclonal and monoclonal antibodies. Several methods have been described for the preparation of antibodies (see e.g., Kohler et al., *Nature,* 256:495-497 (1975)) and *Eur. J. Immunol.* 6:511-519 (1976)); Milstein et al., *Nature* 266:550-552 (1977)); U.S. Pat. No. 4,172,124; Harlow, E. and D. Lane, 1988, *Antibodies: A Laboratory Manual*, (Cold Spring Harbor Laboratory: Cold Spring Harbor, N.Y.); and *Current Protocols In Molecular Biology*, Vol. 2 (Supplement 27, Summer '94), Ausubel, F. M. et al., Eds., (John Wiley & Sons: New York, N.Y.), Chapter 11, 1991); the teachings of each of which are incorporated herein by reference). The term "antibody" encompasses monoclonal antibodies, polyclonal antibodies, humanized antibodies, chimeric antibodies, single-chain Fv (scFv), Fab fragment, F(ab') fragments, intrabodies, and synthetic antibodies. The term "small molecule" as used herein, is meant to refer to a chemical compound which has a molecular weight of less than about 5 kD. Small molecules can be an organic or inorganic chemical compounds.

The agent can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

For parenteral administration, pharmaceutical compositions or pharmacologic agents can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The compositions can be prepared as injectable formulations, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, *Science* 249:1527, 1990 and Hanes, *Advanced Drug Delivery Reviews* 28:97-119, 1997. The compositions and pharmacologic agents described herein can be administered in the form of a depot injection or implant preparation which can be formulated in such a manner as to permit a sustained or pulsatile release of the active ingredient.

The invention also contemplates a method of treatment comprising administering to said patient a pharmacologic agent that increases the flexibility of the veins and/or arteries, and further comprising achieving in said patient an intraventricular pressure (or CSF pressure) below the intraparenchymal venous pressure of the brain. As will be understood by the skilled artisan, the intraventricular pressure can be decreased below the intraparenchnymal venous pressure by decreasing the CSF pressure and/or increasing the intraparenchymal venous pressure. In one aspect of the invention, the CSF pressure is decreased by implanting a shunt into the brain of the patient. In another aspect, the venous pressure of the brain is increased by introducing the patient to a hyperbaric environment, wherein said hyperbaric environment has a pressure greater than atmospheric pressure, and simultaneously venting the CSF from the ventricles to the exterior of the hyperbaric environment. For example, when the hyberbaric environment is a hyberbaric chamber, the CSF is vented from the ventricles to the exterior of the hyperbaric chamber at atmospheric pressure. In some embodiments, the CSF is vented to the exterior of the hyberbaric chamber using a catheter that vents the CSF at the spine (e.g., a spinal tap) to the outside of the chamber, or wherein the CSF is vented directly from the ventricles to the outside of the chamber.

As described above, the intraventricular pressure or the CSF pressure can be decreased by implantation of a shunt that drains CSF from the ventricles into another part of the body where it can be absorbed by the circulation (such shunts are also referred to herein as ventricular shunts). CSF shunts include, for example, ventriculoperitoneal, ventriculopleural and ventriculoatrial shunts. Non-limiting examples of such shunts are described, for example, in U.S. Pat. Nos. 3,288,142, 3,516,410, 3,527,226, 3,877,137, 3,886,948, 3,889,687, 3,958,562, 4,106,510, 4,312,293, 4,332,255, 4,387,715, 4,551,128, 4,595,390, 4,608,992, 4,615,691, 4,772,257, 5,928,182 and in Pujari et al. (2008), J Neurol Neurosurg Psychiatry 79:1282-1268 and Vaneste et al. (1992), Neurology 42 (1): 54-9, the contents of each of which are expressly incorporated by reference herein. These shunts are usually comprised of a cerebral catheter inserted through the brain into the ventricle and a one-way valve system that drains fluid from the ventricle into a reservoir of the body. After surgical implantation of the shunt, the pressure of the valve is set equal to the patient's pre-surgery ventricular CSF pressure so that a pressure change does not occur immediately after surgery. Once the patient has recovered from the surgery, the pressure of the valve is decreased in order to reduce the size of the ventricles. Once the ventricles have reduced sufficiently, the pressure of the valve is then increased to prevent further shrinking of the ventricles. Because patients often require several pressure adjustments after implantation of the shunt, externally programmable valves are commonly utilized. One such example of an externally programmable valve is a differential pressure valve which can be adjusted non-invasively by the clinician using an externally applied rotating magnetic field. Several externally programmable shunts are commercially available and include, for example, the Codman Hakim Programable Valves (Codman, Raynham, MA) and Medronic Strata valves.

In another example, the CSF pressure can be decreased by lumbar drainage.

As described above, the intraventricular pressure can be reduced relative to the intraparenchymal venous pressure of the brain by increasing the venous pressure of the brain. In one aspect of the invention, the intraparenchymal venous pressure of the brain can be increased by introducing the patient to a hyperbaric environment while concomitantly equilibrating the CSF pressure with atmospheric pressure or while venting the CSF from the ventricles to the exterior of the hyperbaric environment as described above. The patient's CSF pressure can be equilibrated with atmospheric pressure, for example, by lumbar puncture wherein the spinal needle is open to atmospheric pressure, for example, by means of a tube or catheter vented to an environment of atmospheric pressure. As used herein, a hyperbaric environment is an environment that has a pressure greater than atmospheric pressure. An example of a hyperbaric environment is a hyperbaric chamber. A hyperbaric chamber is a sealed chamber or compartment in which one or more individuals can enter. The use of hyperbaric chambers has been described for the treatment of decompression sickness, carbon monoxide poisoning, and wound healing. In one aspect of the invention, the hyperbaric chamber is a monoplace hyperbaric chamber. The pressure of the hyperbaric chamber can be adjusted to a pressure sufficient to increase the venous pressure of the brain. In some aspects, the hyperbaric chamber has a pressure that is increased, for example, to about 250 to about 350 mm $H_2O$ above atmospheric pressure. The patient can remain in the hyperbaric chamber for at least about 30 to about 60 minutes. In certain embodiments, the gas flowing into the chamber is oxygen.

Venous pressure of the brain can also be increased using mechanical means.

The invention is also directed to a method of treating a patient suffering from a disorder of the central nervous system comprising introducing said patient to a hyperbaric environment. The introduction of the patient into a hyperbaric environment can also be conducted in combination with implantation of a ventricular shunt. It will be understood that the shunt can be implanted before or after the patient is introduced to the hyperbaric environment. In certain aspects of the invention, the patient is implanted with a ventricular shunt and some time after implantation of the shunt, the patient is introduced into the hyperbaric environment for a time and under conditions suitable to decrease the size of the ventricles. This method can be especially useful in the case where a patient's ventricles do not sufficiently reduce in size after implantation of shunt. Such patients may benefit from combined treatment of CSF pressure reduction (via the ventricular shunt) and venous pressure increase (via the hyperbaric environment).

The present invention also encompasses methods of diagnosing a disorder of the central nervous system in a patient. In one aspect, the disorder of the central nervous system is diagnosed by detecting decreased flexibility or fibrosis of the subarachnoid veins, or detecting a marker thereof. In yet another aspect, the disorder of the central nervous system is diagnosed by detecting the presence of collagen deposition on the walls of the subarachnoid veins and/or arteries, or on the vessels of the eye. Collagen deposition can be visualized under polarized light. Thus, in one example, collagen deposition on the vessels of the eye can be detected during fundoscopic examination using polarized light. In certain embodiments, the diagnosis is made based on the patient's symptoms as well as the detection of collagen deposition on the walls of the subarachnoid veins and/or arteries, or on the vessels of the eye, or the detection of a marker thereof. In a further aspect, the invention comprises increasing the intraparenchymal venous pressure in a patient and monitoring said patient for an improvement in symptoms. Persons of skill in the art are familiar with methods of monitoring patients for an improvement in symptoms associated disorders of the central nervous system. For example, NPH is currently identified in patients by CSF fluid diversion by lumbar puncture and drainage and monitoring the patient for an improvement in symptoms (Verees et al. (2004)). In some aspects, the intraparenchymal venous pressure can be increased by introducing the patient to a hyberbaric environment. In some embodiments, the patient is suspected of suffering from NPH. In other embodiments, the patient is suspected of suffering from Alzheimer's disease. In yet other embodiments, the patient is suspected of suffering from a dementia.

The invention encompasses a method of treating a disorder of the central nervous system in a patient in need thereof comprising mechanically increasing the pulse amplitude in the cranial cavity of said patient, wherein the increase in pulse amplitude is sufficient to increase the flow of waste products from the brain tissue into the extracellular space and CSF. In some embodiments, the patient is suffering from NPH. In other embodiments, the patient is suffering from Alzheimer's disease. In yet other embodiments, the patient is suspected of suffering from a dementia.

Figure 20:
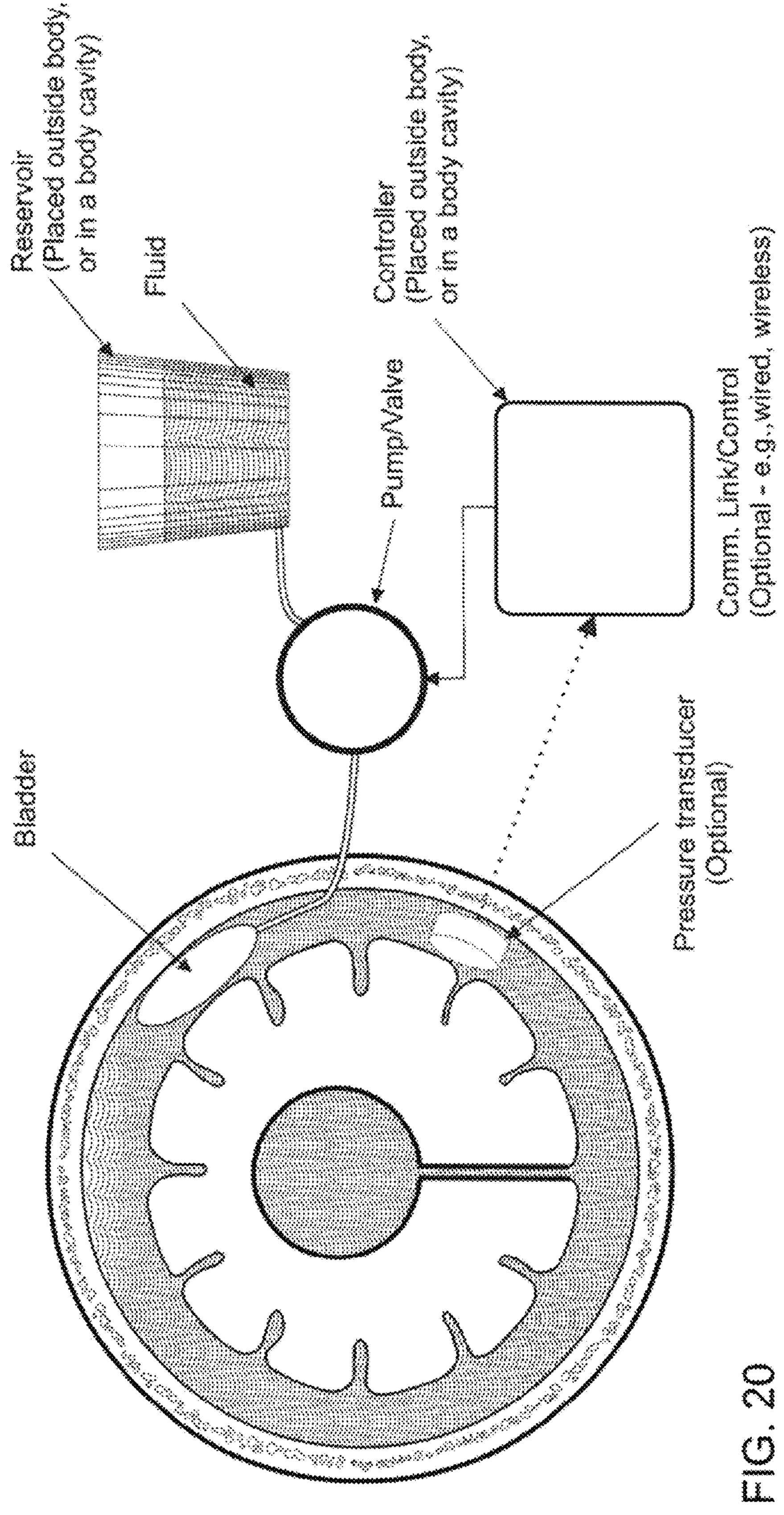
FIG. 20 is diagram illustrating an additional technique of providing a pressure actuator, or pressure trigger, within the cranial cavity. When activated, the pressure trigger causes an increase in pressure within the cranial cavity and improves the "pumping or squeezing" mechanism by which the waste products are eliminated from the brain tissue due to the dampening caused by the hardened vessels of the subarachnoid space.

The invention is further directed to a method for the treatment of a disorder of the central nervous system in a patient in need thereof comprising increasing the pressure of at least a portion of the cranial cavity of said patient by providing a pressure actuator, or pressure trigger within the cranial cavity. When the pressure trigger is activated, the pressure trigger causes an increase in the pressure of at least a portion of the cranial cavity. In one example, a bladder can be placed within the subarachnoid space wherein the interior volume of the bladder is in fluid communication with a reservoir storing a fluid and/or a gas. A pump, a valve, or a combination thereof, is also provided to control the flow of the fluid and/or gas between the bladder and the reservoir. The pump and/or valve can, for example, be operated by a controller, such as a microprocessor, to cause a controlled flow of the fluid and/or gas between the reservoir and the bladder, thereby causing a change in volume of the bladder. The flow of the fluid and/or gas into the bladder will result in an increase in the volume of the bladder. Likewise, the flow of the fluid and/or gas out of the bladder will result in a decrease in the volume of the bladder. The volumetric change of the bladder occurring within the enclosed, rigid volume of the cranial cavity causes a corresponding change in pressure within the cranial cavity. In particular, the exchange of the fluid and/or gas between the reservoir and the bladder can be controlled in a periodic manner to simulate, augment, or substitute the natural pulsation of the brain resulting from healthy systolic pressure. One or more of the reservoir, the controller, pump, etc., can be surgically implanted, or located outside of the body. FIG. 20 illustrates an example of a pressure controlling device.

As discussed above, the invention encompasses a method for the treatment of a disorder of the central nervous system in a patient in need thereof, comprising diagnosing the patient as possessing a predisposition condition characterized by a pre-disposition for decreased flexibility of the subarachnoid veins and/or arteries, such as a disorder of the central nervous system; and administering to the patient a pharmacologic agent that increases the flexibility of the veins or arteries, or a combination thereof, in the subarachnoid space of the brain of said patient, wherein the pharmacologic agent is administered in an amount effective to inhibit the, the hardening of the subarachnoid veins and/or arteries. Method of determining patients possessing a predisposition of suffering from a disorder of the central nervous system will be well-known to those of skill in the art. For example, the patient can be assessed for a pre-disposition for Alzehimer's disease which can involve, for example, gene risk profiling, monitoring proteins in the cerebrospinal fluid (e.g., Alzheimer's disease in its earliest stages may cause changes in CSF levels of tau and beta-amyloid), monitoring proteins in a biological sample such as the blood or urine (for example, measuring urine or blood levels of tau, beta-amyloid or other biomarkers) and imaging to detect brain changes (for example, radiotracers such as 18F flutemetamol, Florbetapir F 18, Florbetaben) capable of highlighting deposits of beta-amyloid (e.g., using PET scan), and monitoring for mild cognitive impairments.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of diagnosing a disorder of the central nervous system (CNS) associated with decreased flexibility of subarachnoid veins, arteries, or both in a patient having an initial intraparenchymal venous pressure (Pv) below normal and an initial cerebrospinal fluid (CSF) pressure ($P_{CSF}$) with a gradient such that Pcsf>Pv, the method comprising:

imaging the subarachnoid veins, arteries, or both of the patient or vessels of an eye of the patient to detect any presence of collagen deposition, the imaging comprising performing a fundoscopic exam using polarized light;

treating the patient to increase the intraparenchymal venous pressure from the initial pressure below normal to a second pressure greater than the initial pressure, while maintaining the CSF pressure at the initial CSF pressure or decreasing the CSF pressure to a second CSF pressure less than the initial CSF pressure in the patient such that $P_{CSF}$=Pv or Pv>$P_{CSF}$, wherein treating the patient increasing the intraparenchymal venous pressure comprises monitoring $P_{CSF}$ and Pv of the patient and at least one of introducing the patient to a hyperbaric environment for a time and under conditions suitable for increasing the intraparenchymal venous pressure to the second pressure, or operating a pressure actuator comprising a bladder implanted in a cranial cavity of the patient in fluid communication with a reservoir storing a fluid and/or gas, and a pump and/or valve operably connected to control flow of the fluid and/or gas between the bladder and the reservoir, to control pressure;

assessing whether the patient has exhibited any improvement of symptoms associated with the disorder of the CNS; and responsive to the detection of collagen deposition in the imaging and assessment of improvement of symptoms, diagnosing the patient as having the disorder of the CNS.

2. The method of claim 1, further comprising illuminating with polarized light an exterior layer of the veins during the fundoscopic exam, detecting optical activity upon the illumination, and diagnosing the patient with the disorder of the CNS responsive to the detected optical activity, wherein the disorder of the CNS is normal pressure hydrocephalus (NPH).

3. The method of claim 1, which comprises detecting collagen deposition in adventitia of the subarachnoid veins.

4. The method of claim 1, which comprises detecting collagen deposition in adventitia of the subarachnoid arteries.

5. The method of claim 1, wherein the disorder of the central nervous system is normal pressure hydrocephalus (NPH) or Alzheimer's disease.

6. The method of claim 1, comprising introducing the patient to the hyperbaric environment and further comprising venting CSF from ventricles of the patient to an exterior of the hyperbaric environment.

7. The method of claim 1, wherein symptom improvement comprises alleviating one or more of motor disturbance, incontinence, dementia, and ventricular enlargement in the absence of elevated intracranial pressure.

8. The method of claim 1, further comprising implanting into the brain of the patient a shunt configured to drain the CSF from the ventricles prior to introducing the patient into the hyperbaric environment.

9. A method of diagnosing normal pressure hydrocephalus (NPH) in a patient having an initial intraparenchymal venous pressure (Pv) below normal and an initial cerebrospinal fluid (CSF) pressure ($P_{CSF}$) with a gradient such that Pcsf>Pv, the method comprising:

imaging the subarachnoid veins, arteries, or both of the patient or vessels of an eye of the patient to detect any presence of collagen deposition, the imaging comprising performing a fundoscopic exam using polarized light;

treating the patient to increase the intraparenchymal venous from the initial pressure below normal to a second pressure greater than the initial pressure, while maintaining er decreasing cerebrospinal fluid (CSF) the CSF pressure at the initial CSF pressure or decreasing the CSF pressure to a second CSF pressure less than the initial CSF pressure in the patient such that PCSF=Pv or Pv>Pcsf, wherein treating the patient increasing the intraparenchymal venous pressure of the patient comprises monitoring Pcsf and Pv of the patient and at least one of introducing the patient to a hyperbaric environment for a time and under conditions suitable for increasing the intraparenchymal venous pressure to the second pressure, administering to the patient intrathecally or intracerebroventricularly an effective amount of a pharmacologic agent encapsulated in a liposome to increase flexibility of the veins, arteries, or both, the pharmacologic agent comprising an anti-fibrotic agent or an agent capable of inhibiting collagen accumulation or degrading collagen on the veins, arteries, or a combination thereof, selected from aprotinin, cis-hydroxyproline (cHYP), hepatocyte growth factor, phorbol 12-myristate 13-acetate, or L-azetidine-2-carboxylic acid; or operating a pressure actuator comprising a bladder implanted in a cranial cavity of the patient in fluid communication with a reservoir storing a fluid and/or gas, and a pump and/or valve operably connected to control flow of the fluid and/or gas between the bladder and the reservoir, to control pressure in an amount effective to increase pulse amplitude in the cranial cavity;

assessing whether the patient has exhibited any improvement of symptoms associated with NPH; and responsive to the detection of collagen deposition in the imaging and assessment of improvement of symptoms, diagnosing the patient as having NPH.

10. The method of claim 9, comprising introducing the patient to the hyperbaric environment and further comprising venting CSF from ventricles of the patient to an exterior of the hyperbaric environment.

11. The method of claim 9, wherein symptom improvement comprises alleviating one or more of motor disturbance, incontinence, dementia, and ventricular enlargement in the absence of elevated intracranial pressure.

12. The method of claim 9, further comprising implanting into the brain of the patient a shunt configured to drain the CSF from the ventricles prior to introducing the patient into the hyperbaric environment.

13. A method of diagnosing normal pressure hydrocephalus (NPH) in a patient having an initial intraparenchymal venous pressure (Pv) below normal and an initial cerebrospinal fluid (CSF) pressure ($P_{CSF}$) with a gradient such that Pcsf>Pv, the method comprising:

imaging the subarachnoid veins, arteries, or both of the patient or vessels of an eye of the patient to detect any presence of collagen deposition, the imaging comprising performing a fundoscopic exam using polarized light;

monitoring $P_{CSF}$ and Pv of the patient;

treating the patient to increase the intraparenchymal venous from the initial to a second pressure greater than the initial pressure, while maintaining the CSF pressure at the initial CSF pressure or decreasing the CSF pressure to a second CSF pressure less than the initial CSF pressure in the patient such that $P_{CSF}$=Pv or Pv>$P_{CSF}$, wherein increasing the intraparenchymal venous pressure of the patient to the second pressure comprises administering to the patient intrathecally or intracerebroventricularly an effective amount of a pharmacologic agent encapsulated in a liposome to increase flexibility of the veins, arteries, or both, the pharmacologic agent comprising an anti-fibrotic agent or an agent capable of inhibiting collagen accumulation or degrading collagen on the veins, arteries, or a combination thereof, selected from aprotinin, cis-hydroxyproline (cHYP), hepatocyte growth factor, phorbol 12-myristate 13-acetate, or L-azetidine-2-carboxylic acid;

assessing whether the patient has exhibited any improvement of symptoms associated with NPH; and responsive to the detection of collagen deposition in the imaging and assessment of improvement of symptoms, diagnosing the patient as having NPH.

14. The method of claim 13, further comprising illuminating with polarized light an exterior layer of the veins during the fundoscopic exam, detecting optical activity upon the illumination, and diagnosing the patient with the disorder of the CNS responsive to the detected optical activity.

15. The method of claim 13, wherein symptom improvement comprises alleviating one or more of motor disturbance, incontinence, dementia, and ventricular enlargement in the absence of elevated intracranial pressure.

* * * * *